United States Patent [19]

Sheehan et al.

[11] Patent Number: 5,404,885
[45] Date of Patent: Apr. 11, 1995

[54] FILTER UNIT FOR END-TIDAL CARBON MONOXIDE MONITOR

[75] Inventors: Neil J. Sheehan, Palo Alto; Scott R. Rouw, Union City; Robert T. Stone, Sunnyvale, all of Calif.

[73] Assignee: Natus Medical, Incorporated, San Carlos, Calif.

[21] Appl. No.: 184,379

[22] Filed: Jan. 21, 1994

Related U.S. Application Data

[60] Division of Ser. No. 990,425, Dec. 15, 1992, abandoned, which is a continuation-in-part of Ser. No. 899,261, Jun. 16, 1992, Pat. No. 5,293,875.

[51] Int. Cl.$^6$ .............................................. A61B 5/08
[52] U.S. Cl. ..................... 128/716; 128/719; 128/204.22; 422/83; 73/23.3
[58] Field of Search ............ 128/716, 719, 204.22, 128/204.23, 205.22; 422/83, 84; 73/23.3

[56] References Cited

U.S. PATENT DOCUMENTS

| | | | |
|---|---|---|---|
| 3,977,394 | 8/1976 | Jones et al. | 128/2.07 |
| 4,304,578 | 12/1981 | Hakala et al. | 128/719 |
| 4,423,739 | 1/1984 | Passaro et al. | 128/719 |
| 4,821,737 | 4/1989 | Nelson | 128/719 |
| 4,831,024 | 5/1989 | Vreman et al. | 514/185 |
| 4,870,961 | 10/1989 | Barnard | 128/205.12 |
| 4,886,528 | 11/1989 | Aaltonen et al. | 128/719 |
| 4,968,887 | 11/1990 | Wong | 250/343 |
| 5,003,985 | 4/1991 | White et al. | 364/413.03 |

OTHER PUBLICATIONS

Yeung et al., "Automatic End Expiratory Air Sampling Device For Breath Hydrogen Test In Infants", *The Lancet*, vol. 337, pp. 90–93 (Jan. 12, 1991).
Product Literature—Z World Engineering Little Giant Miniature Microcontroller (One page).
Product Literature—Servomex Mode 1505 Co2 Infrared Transducer brochure (2 pages) and technical note (9 pages).
Product Literature—KNF Diaphragm Micro Pump Type NMP 02 (2 pages).

*Primary Examiner*—Lee S. Cohen
*Assistant Examiner*—Robert L. Nasser, Jr.
*Attorney, Agent, or Firm*—Davis, Hoxie, Faithfull & Hapgood

[57] ABSTRACT

A noninvasive device and methods for measuring the end-tidal carbon monoxide concentration in a patient's breath, particularly newborn and premature infants. The patient's breath is monitored. An average carbon monoxide concentration is determined based on an average of discrete samples in a given time period. The ratio of the end-tidal portion of the breath flow sample is separately determined, preferably based on monitoring the level of carbon dioxide in the gas sample and identifying the carbon dioxide concentration levels corresponding to the end-tidal portion of the breath sample. The sensed carbon monoxide level is converted to the end-tidal carbon monoxide level by subtracting the ambient carbon monoxide level and dividing the remainder by the ratio of end-tidal breath to breath in the breath sample. An easy to use microcontroller-based device containing a carbon dioxide detector, a carbon monoxide detect and a pump for use in a hospital, home, physician's office or clinic by persons not requiring high skill and training is described. A replaceable filter unit made of a single tri-lumen PVC extrusion and a tube segment inter-connecting two of the lumens used to provide the consumable filtration material. The filtration material is interposed between the carbon dioxide sensor and the carbon monoxide sensor which are mounted inside the monitor housing. The filter unit also interfaces the canula for receiving the patient's breath sample and a hydrophobic filter between the patient and the carbon dioxide monitor.

16 Claims, 11 Drawing Sheets

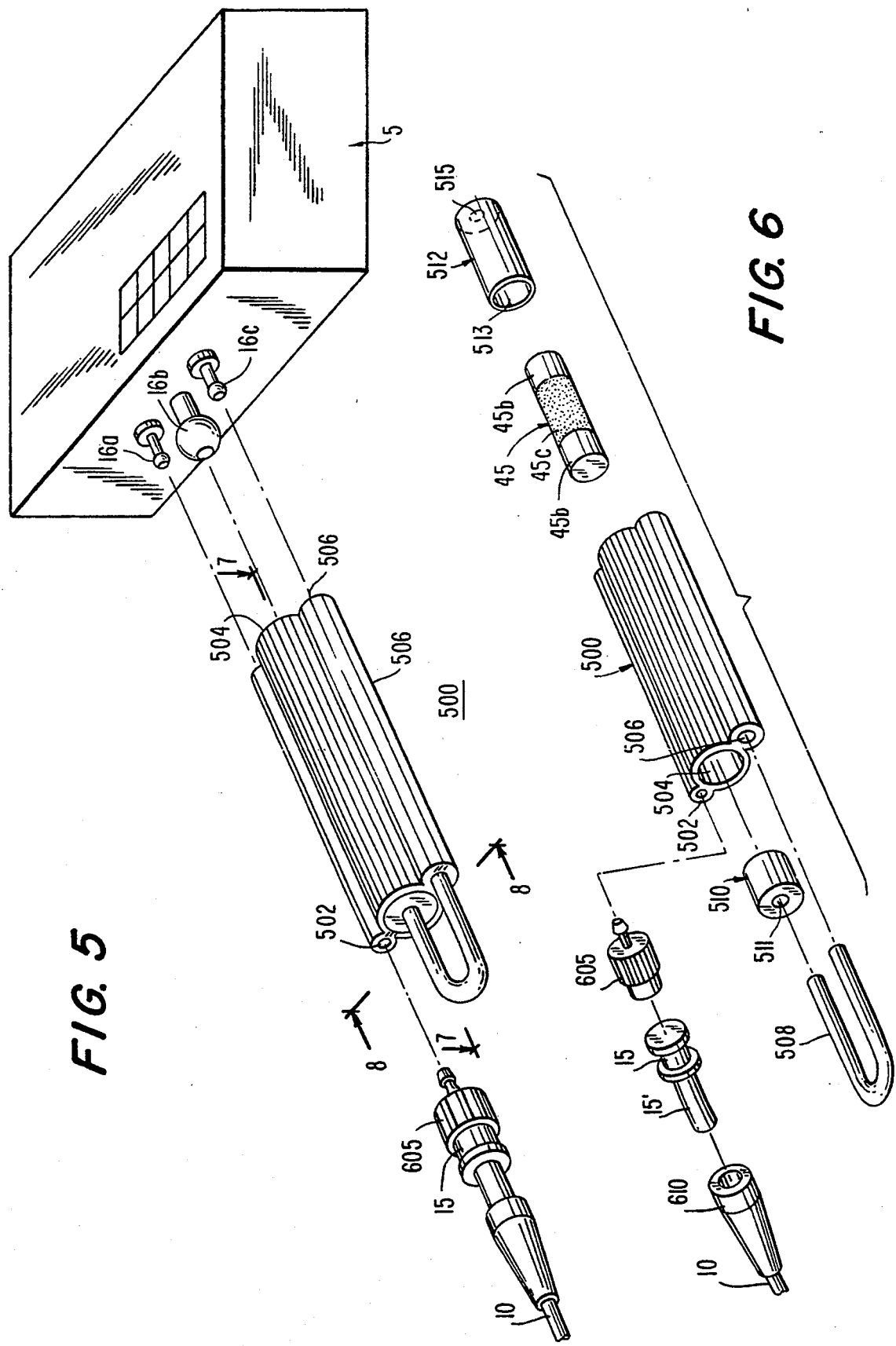

FILTER UNIT FOR END-TIDAL CARBON MONOXIDE MONITOR

CROSS REFERENCE TO RELATED APPLICATIONS

This is a divisional of U.S. Pat. application No. 07/990,425, filed Dec. 15, 1992, now abandoned, which is a continuation-in-part of U.S. Pat. application 07/899,261, filed Jun. 16, 1992, now U.S. Pat. No. 5,293,875.

FIELD OF THE INVENTION

This invention relates to methods and apparatus for invivo, real time measurement of end-tidal carbon monoxide concentration in the exhaled breath, more particularly to a filter unit for use in the determination of end-tidal carbon monoxide concentration in the breath of a newborn infant.

BACKGROUND OF THE INVENTION

In most animal systems, carbon monoxide is a waste product produced in the breakdown of free hemoglobin within the blood. Ordinarily, hemoglobin is contained within red blood cells and is stable. However, aging of red blood cells and certain disease processes produce hemolysis, i.e., the breakdown of the cell wall. This produces free hemoglobin which breaks down in the blood. The carbon monoxide that is produced by the breakdown of free hemoglobin is normally excreted in the breath.

When the system is in equilibrium, the carbon monoxide concentration in the breath is proportional to the difference in the concentration of carbon monoxide in the blood and the concentration of carbon monoxide in room air. This difference in concentration is proportional to the rate of hemolysis in the blood.

The concentration of carbon monoxide in the end-tidal breath, i.e., the gas that is last expelled each breath, is presumed to be at equilibrium with the concentration in the blood. This is because the end-tidal breath contains predominantly, if not exclusively, the gas expelled from the alveoli in the lungs, which gas was within the alveoli for a time generally sufficient to equilibrate with the blood.

It is known that hemolysis and the resulting by-products and consequences of hemolysis can be estimated or predicted from a measure of the concentration of carbon monoxide in the end-tidal breath. See Smith, D. W. et al., "Neonatal Bilirubin Production Estimated from End-Tidal Carbon Monoxide Concentration", *Journal of Pediatric Gastroenterology and Nutrition*, 3:77–80, 1984.

One method of analysis previously reported includes incrementally acquiring a sample of end-tidal breath and analyzing the acquired sample by mass spectroscopy or gas chromatography to determine the end-tidal carbon monoxide concentration. The sample is obtained by extracting from each of several successive breaths a portion of the apparent end-tidal breath using a syringe. The end-tidal portion of breath is determined by observing the chest movements of the infant. See, e.g., Vreman et al. U.S. Pat. No. 4,831,024.

One problem with this technique is that it requires a skilled, trained user to obtain the end-tidal sample in successive increments based on watching chest wall movements. It also requires a trained, skilled person to operate a complex piece of analytical laboratory equipment to analyze the acquired sample. In addition, this technique requires time and personnel to transport the sample from the patient to the laboratory (or equipment) where the analysis is conducted, and then to report back to the attending physician/practitioner for a diagnosis and prescription, if any.

Another problem with this technique is that accurate assessment of the concentration difference in carbon monoxide requires obtaining good samples of end-tidal patient breath. This essentially requires that the patient have a regular, predictable breathing cycle. Thus, it can be difficult to obtain a good sample by watching chest wall movement, particularly for a newborn and for patients having irregular breathing cycles.

Chemical electrochemical sensors capable of measuring carbon monoxide concentrations in the range of interest, 0 to 500 parts per million (ppm), are commercially available, e.g., model DragerSensor CO available from Dragerwerk, Lubeck, Germany. However, such sensors are sensitive to many other gases as well as carbon monoxide, and are therefore susceptible to error. Another problem with such sensors is that the measurement dynamics of the sample gas transport through the gas permeable membrane and oxidation-reduction in the electrochemical cell results in a relatively slow response time such that discrete samples of the end-tidal breath must be obtained and analyzed to determine the end-tidal carbon monoxide concentration.

SUMMARY OF THE INVENTION

It is, therefore, an object of the present invention to provide improved non-invasive apparatus and methods for measuring carbon monoxide concentration in the end-tidal breath. It is another object to provide apparatus and methods that operate in real-time. It is another object to provide apparatus and methods for use in determining the rate of hemolysis from the concentration of end-tidal carbon monoxide.

It is another object of the present invention to provide apparatus and methods for measuring end-tidal carbon monoxide that do not require a highly skilled, trained individual to obtain and determine the measure. It is another object to provide such apparatus and methods that do not require incrementally acquiring samples of end-tidal breath during successive respiratory cycles.

It is another object of the invention to provide a portable, easy-to-use apparatus that can be used in a nursery, a physician's office, a hospital, a clinic, and a mobile clinic for measuring end-tidal carbon monoxide in real-time, for assessing the likelihood of elevated levels of hemolysis for immediate entry on the patient's record and prescription of an appropriate remedy.

It is another object of this invention to provide an end-tidal carbon monoxide monitor with a replaceable filter unit for use with different patients, and for replacing consumed gas filtering components. It is another object to provide an inexpensive disposable filter unit.

It is another object of this invention to provide keyed bulkhead fittings on the monitor for receiving the filter in the correct orientation and to provide for proper flow path interconnection and operation of the disposable filter in the monitor.

In accordance with this invention, there is provided an apparatus, sampling methods, and analysis techniques for measuring the concentration of end-tidal carbon monoxide in breath, particularly in newborn and premature infants. Broadly, the invention concerns determining the concentration of end-tidal carbon monoxide based on a measure of the room air carbon monoxide concentration, a measure of the average carbon monoxide concentration for a breath sample over a period of time, and a determined ratio of the end-tidal breath to inspired air for the sampled portion.

The present invention is based in part on the discovery that accurate assessment of end-tidal carbon monoxide concentration may be obtained based on knowledge of the fraction of the gas sample that is end-tidal gas. Thus, the present invention is able to avoid selectively sampling small samples of end-tidal breath over successive respiratory cycles to obtain a sufficiently large end-tidal breath sample, which incremental sampling is problematic. Further, the invention advantageously uses a conventional carbon monoxide detector, which has a response time that is not fast enough to distinguish carbon monoxide in end-tidal breath from carbon monoxide in inspired air, to derive the end-tidal carbon monoxide concentration in real-time. More particularly, a conventional carbon monoxide detector can be used to obtain the average carbon monoxide concentration level during breathing, which average value can be related to the end-tidal value based on the determined ratio of end-tidal to inspired breath. Preferably, the most common interfering substances from a sampled breath are removed from the sample by a consumable filtration medium so that these substances do not affect the measurement. The present invention also applies to gas components of exhaled breath other than carbon monoxide, which gas components cannot be directly monitored because of the slow response time of available gas detectors.

One aspect of the present invention concerns using a second gas component of the breath, other than the first gas component whose concentration is being monitored, to determine the ratio of the end-tidal breath to inspired air. The relative concentration level of the second gas during respiration is monitored and the ratio or duty cycle of the end-tidal portion of the sensed concentration waveform relative to the inspired air is determined. A sensor for detecting the level (or concentration) of the second gas having a time response that is fast enough to distinguish the end-tidal breath concentration from the inspired air is preferably used. One suitable gas component is carbon dioxide, which has a large, distinctive change in concentration with breathing. Other gases may be used, e.g., hydrogen, oxygen, or some combination of gases, e.g., carbon dioxide and hydrogen.

The determined end-tidal carbon monoxide concentration may be used by a physician or other suitable health care provider to evaluate the rate or relative level of hemolysis occurring in the infant. The evaluation is typically made by comparing the determined end-tidal carbon monoxide concentration to known or preselected standards. For example, when measured soon after birth, the end-tidal carbon monoxide range 0.6–1.9 $\mu l/l$ is considered normal and the range above about 2 $\mu l/l$ is considered at risk. Premature infants have both a higher risk of neonatal jaundice and a higher normal range of end-tidal carbon monoxide.

Another aspect of the present invention concerns a disposable filter unit that contains the consumable filtration medium. One embodiment of this aspect of the invention provides an assembly to direct the gas flow through the monitor having two distinct flow paths. One flow path provides for receiving the breath flow sampled at the patient into the monitor, more specifically, from the nasal canula to the carbon dioxide detector. The second flow path contains the consumable filtration medium and provides a flow path between the carbon dioxide sensor and the carbon monoxide sensor.

In a preferred embodiment, the assembly is formed of a body having three flow paths (also called lumens) extending from one end to the other and a tube segment that is used to connect two of the flow paths at one end of the body. The consumable filtration medium is located in one of the two lumens connected by the tube segment. Thus, the tube segment provides for a gas flow path from the carbon dioxide detector, through the consumable filtration medium, and to the carbon monoxide detector. Preferably, the three lumens are straight and have longitudinal axes that are in the same plane. More preferably, the three lumens have different interior dimensions and respectively mate to corresponding differently sized bulkhead fittings on the monitor. This ensures that the filter unit will be installed in the correct orientation with tight interconnections.

In the preferred embodiment, the body and its lumens are formed by coextrusion of a single piece of plastic material, e.g., soft polyvinyl chloride. The consumable filtration medium is then inserted in one of the lumens of the second flow path. A plug is inserted into the distal end of that lumen, which has a flow passageway extending through the plug for receiving a length of the tube segment.

The piece of tubing is bent into a U-shape to interconnect the two selected lumens. In this regard, the tube segment preferably has an outer diameter that provides an air tight frictional fit when it is inserted in the plug flow passageway and the other lumen of the second flow path. Preferably, the tubing has interior ribs along its length to minimize the likelihood of the tube collapsing or pinching closed when it inserted in the paths. The tube segment is preferably secured to each of the plug flow passageway and the other lumen, which are of about the same inner dimension (diameter), by a conventional solvent dipping and bonding process.

Another aspect of the invention is directed to providing a hydrophobic filter that plugs into the distal end of the lumen of the filter unit forming the first flow path. A conventional fitting for receiving the hydrophobic filter is interposed between the canula tubing that is used to take the breath sample from the patient and the filter unit. This construction is particularly advantageous because the filter and fitting elements are quickly and easily assembled by the end user, and alternately can be provided in a preassembled configuration in a clean, but not necessarily sterile package. In addition, it also is extremely low cost because it uses a combination of conventional commercial parts.

The present invention provides a tool for predicting the likelihood that the determined level of hemolysis will lead to adverse consequences, such as jaundice and hyperbilirubinemia, which might not appear for several days. Thus, the apparatus and methods of the present invention provide for reliable detection and early treatment of the condition by an appropriate remedy, and for monitoring the efficacy of the treatment.

BRIEF DESCRIPTION OF THE DRAWINGS

The above and other objects and advantages of the invention will be apparent upon consideration of the following detailed description taken in conjunction with the accompanying drawings, in which like reference characters refer to like parts throughout, and in which:

FIG. 5 is an elevated perspective view of a filter unit in accordance with a preferred embodiment of the invention;

FIG. 6 is an exploded isometric view of the filter of FIG. 5;

DETAILED DESCRIPTION OF THE INVENTION

Figure 1:
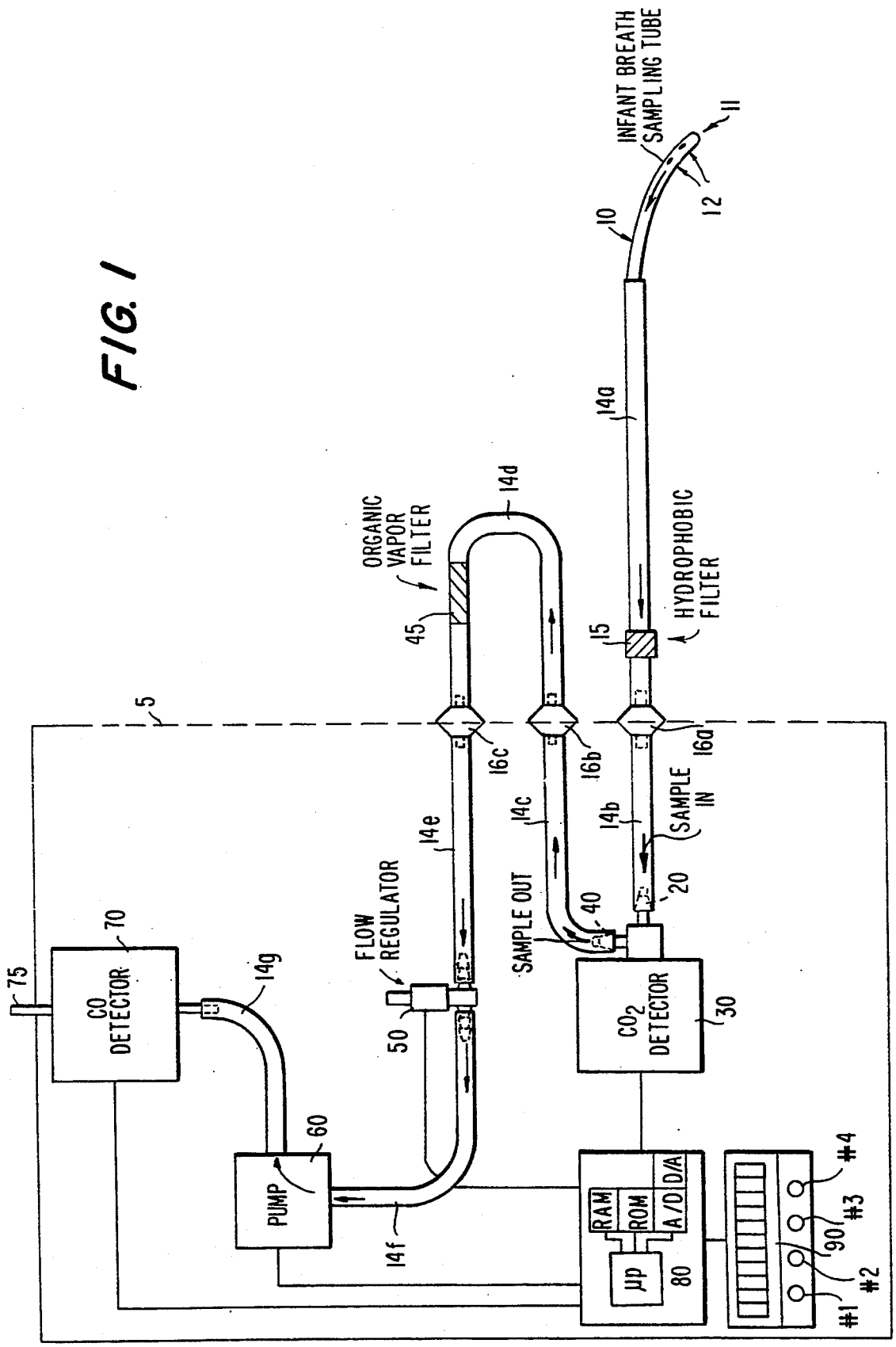
FIG. 1 is a schematic block diagram of an apparatus for determining end-tidal carbon monoxide concentration in accordance with the present invention.

Referring to FIG. 1, a preferred embodiment of the present invention relates to methods and apparatus for monitoring breath flow of a patient over a period of time and determining the end-tidal concentration of carbon monoxide in the breath. The apparatus includes a nasal cannula 10, a carbon dioxide detector 30, an organic vapor filter 45, a flow regulator 50, a pump 60, a carbon monoxide detector 70, and a microcontroller 80. Preferably, a hydrophobic filter 15 is provided between the cannula 10 and the gas detectors to remove moisture from the sample of breath. In particular, filter 15 is used so that moisture does not interfere with detecting carbon dioxide. Filter 15 is illustrated in FIG. 1 as inserted between tube 14a, which includes cannula 10, and a connector 16a, which is secured to the base 5 which supports and preferably encloses the gas detectors 30 and 70, pump 60, and flow regulator 50. One suitable hydrophobic filter 15 is part number 51190, available from Filtertek, Inc.

Cannula 10 is one segment of tubing 14a which has one end 11 that is adapted for insertion into the nostril (posterior nasal pharynx) of a normally breathing patient, e.g., an infant. End 11 has at least one aperture 12 for extracting a sample of the exhaled breath as described below. Preferably, end 11 has a length and an inner and outer diameter appropriate for insertion into the patient's nostril, e.g., a 3.0 cm length of tubing having an inner diameter on the order of 1.0 to 1.5 mm and an outer diameter of 2-3 mm, and a sufficient number of holes 12 perforating the tube circumference for receiving a sample of breath. The dimensions may be adjusted for the size of the patient. The length of cannula 10 is sufficient to extend from the base 5 to the patient, and is typically on the order of 75 to 100 cm.

Segments of tubing 14a, 14b, 14c, 14d, 14e, 14f and 14g are used to form the flow path between the various elements of the apparatus as shown in FIG. 1. The tube segments may be made of, for example, medical grade catheter tubing, polyethylene, polypropylene or vinyl. The ends of the segments are typically frictionally fitted over bosses of connectors 16 and the various components as shown in FIG. 1 and may be clamped for a more secure interconnection. Connectors 16a, 16b, and 16c are preferably mounted in the same region of base 5 to allow for easy access for replacement of the cannula and filters.

Cannula 10 is connected at its other end in series with filter 15, connector 16a, a second length of tubing 14b and the input port 20 of a carbon dioxide detector 30. Detector 30 has a gas sample cell and is used to provide a signal corresponding to the sensed concentration of carbon dioxide in the gas. The detector 30 has a response time that is sufficiently fast to distinguish the concentration level of the end-tidal portion from the other portions of the breath. Thus, the signal changes in response to changes in the concentration of carbon dioxide in the breath as the patient breathes. The resultant signal waveform is used, as described below, to determine the ratio of the end-tidal portion of the breath to the entire inspired air. This ratio, referred to as the duty cycle ("dc") is used to convert the detected carbon monoxide concentration ("CO") to the end.-tidal carbon monoxide concentration ("$CO_{ET}$"), as described below.

One suitable carbon dioxide gas analyzer is the commercially available Servomex model 1505 fast response carbon dioxide infrared transducer, which is available from Servomex Company, 90 Kerry Place, Norwood, Mass. 02062. This device is a temperature compensated, sealed transducer that is based upon a single beam, single wavelength technique absorption for measuring carbon dioxide. It has a complete optical bench and uses a fast infra-red carrier which is attenuated by the infrared absorption of carbon dioxide in the gas. The device has detection circuitry that will convert fast changes of attenuation into an electrical output signal.

The Servomex model 1505 transducer is used in accordance with the manufacturers directions and specifications. It provides, under constant conditions, a linear output voltage of from 0 to 1.0 volts corresponding to from 0 to 10% carbon dioxide, and is extendable up to 1.5 volts corresponding to 15% carbon dioxide. The response time is on the order of 120 ms at a flow of 100 ml/min, and the flow rates may be in the range of from 50-200 ml/min. Other carbon dioxide measuring devices also could be used.

It should be understood that any device that is capable of determining the duty cycle of end-tidal breath to inspired air over a given period of time may be used in place of the carbon dioxide detector, provided that the determined duty cycle is for the same period of time during which the sample on which the carbon monoxide concentration determination is based was acquired. Such a device may be a spirometer for measuring flow velocity or flow volume, a non breath flow device for monitoring breathing, e.g., an impedance pneumograph, a microphone sensor, and the like. Also, a breath gas detector for monitoring a breath gas other than carbon dioxide may be used.

The carbon dioxide detector is preferred because changes in $CO_2$ concentrations related to end-tidal flow are relatively large and easily detectable using a threshold level of carbon dioxide. Further, the same sample of breath can be used to determine the carbon monoxide and carbon dioxide concentrations without affecting the sample, particularly when the sample stream is passed through an infrared absorption-type carbon dioxide detector prior to an electrochemical cell type carbon monoxide detector. In addition the use of an exhaled gas (carbon dioxide or another) provides a non intrusive and non invasive technique for determining the duty cycle dc. It does not require an additional or alternate sensor or transducer on or near the patient and it does not require additional patient cooperation or discomfort. Furthermore, using one time-sample of breath to determine the duty cycle of end-tidal breath is more accurate than visually monitoring chest wall movement or respiratory activity over a period of breathing cycles, or relying on a predetermined breathing rate, which are subject to change, and attempting to obtain samples of exhaled breath only during end-tidal portions.

Other gas sensors may be used, e.g., oxygen which would have a relatively reduced concentration level during end-tidal breath, or hydrogen, which would have a relatively increased concentration level during end-tidal breath. Two different gas detectors, e.g., carbon dioxide and hydrogen, could be used to identify the end-tidal portion, wherein carbon dioxide provides a fast response and hydrogen provides a slow response to changes in concentration.

Another advantage of the invention with respect to relying on changes in gas concentration levels is that the measurement decouples the breath gas concentrations from rhythmic respiratory activity. In other words, pump 60 may be used to provide a gas flow rate through cannula 10 and the flow path that is greater than the patient's respiratory flow. This, in turn, provides an end-tidal "waveform" stretching that enhances evaluation of the gas concentrations and determination of the end-tidal portion of the breath based on a breath gas. It also provides for synchronization between the respiratory activity corresponding to the end-tidal portion based on carbon dioxide and the detection of carbon monoxide concentration in the same breath sample flow. Consequently, the carbon monoxide concentration may be calculated based on post data acquisition processing analysis of the last acquired sample. As a result, the end-tidal carbon monoxide determination is effectively provided in real-time and without the delay occasioned by the previously reported techniques. In addition, the present invention avoids reliance on a previously established breathing cycle or rate to predict when chest wall movement coincides with end-tidal flow. Instead, the invention is completely responsive to changes in the patient's breathing rate and volume as the sample is acquired. The prior known techniques are not.

The gas flow output 40 of detector 30 is in turn connected to a piece of tubing 14c and passed through connector 16b into tube segment 14d. Tube segment 14d contains an organic vapor filter 45. Filter 45 may contain any medium that will absorb organic vapors and reducing gases that might interfere with detecting carbon monoxide levels in the carbon monoxide detector 10.

Filter 45 preferably contains activated charcoal. It is preferably constructed as a canister that either can be inserted interior to the flow path of tube 14d or is inserted between two segments of tubing such that the analyte gas stream passes through the canister. Filter 45 illustrated in FIG. 1 connected between two connectors 16b and 16c so that it is external to base 5. This provides for simple and quick replacement of filter 45 when it is substantially consumed. Filter 45 may be an inexpensive disposable portion of the apparatus.

One advantage to using filter 45 is that it tends to average the concentrations of gas in the analyte stream by thoroughly mixing the stream within the volume of filter 45. A preferred construction of filter 45 is to use a 20 mm length of charcoal rod having a circumference of 24.4 mm which is sandwiched between 3.0 mm segments of white acetate having the same circumference. The charcoal rod is preferably cut from Filtrona AAD Charcoal Filter Rods, available from American Filtrona Corp., Richmond, Va. Where desired, more than one carbon rod segment may be used, provided that pump 60 has sufficient power to pass the analyte gas stream therethrough.

Flow regulator 50 and pump 60 are inserted, preferably in tandem as illustrated in FIG. 1, into or between segments of tubing 14 to maintain a desired constant flow velocity of the analyte stream. Flow regulator 50 is interposed between tubing 14e, which is connected to connector 16c, and tubing 14f, which is connected to pump 60. Pump 60 is in turn interposed between tubing 14f and tubing 14g, which is connected to carbon monoxide detector 70.

Preferably, pump 60 and flow regulator 50 are adjusted so that the flow is maintained at from 40 to 60 ml/min, more preferably 50 ml/min. This provides for withdrawing continuously a gas sample, either from room air or from the patient's posterior nasal pharynx, depending on placement of the cannula 10, including expired and end-tidal breath for patients having a breathing rate of from 10 to 90 breaths per minute. The flow regulator 50 provides for limiting the flow rate of the analyte gas stream, and the pump 60 provides for sampling the gas sample (room air or breath) such that pump 60 is driven against the flow rate limit set by flow regulator 50. This maintains a constant flow rate for the analyte stream, and avoids any flow surges due to a patient's inhalation or expiration. One suitable flow regulator is orifice/needle valve model F-2822-41-B80-55 available from Air Logic, Racine, Wis., which can be adjusted to obtain the desired gas flow rate in the range of 40–60 ml/min. One suitable pump is model NMP 02 diaphragm micro pump, available from KNF Neuberger, Inc, Princeton, N.J., which has a free flow capacity of 0.22 to 0.55 L/min. Pump 60 and flow regulator 50 may be located anywhere in the flow stream, preferably between the carbon dioxide detector 30 and carbon monoxide detector 70 inside the enclosure of base 5. Pump 60 also passes the analyte flow stream out exhaust 75, downstream of the gas detectors 30 and 70 of the apparatus.

Carbon monoxide detector 70 is preferably an electrochemical sensor that produces an electrical current proportional to the concentration of reducing gases, such as carbon monoxide, which are present in the gas, at the gas permeable membrane of detector 70 (not shown). The response time of the carbon monoxide detector 70 and the averaging function of the filter 45 preferably result in a signal output from the detector 70 that is proportional to the average concentration of the reducing gas at the membrane.

One suitable carbon monoxide sensor is model DragerSensor CO, available from Dragerwerke of Lubeck, Germany. It has a plastic gas permeable membrane, a liquid electrolyte, sensing, reference, and counter electrodes in the electrolyte, and a potentiostatic circuit that maintains a constant voltage between the sensing and reference electrodes. The carbon monoxide in the gas is electrochemically converted at the sensing electrode, which produces a current proportional to the carbon monoxide partial pressure. The device is temperature compensated. It has a concentration sensitivity in the range up to 500 ppm and provides an output current of $0.13 \pm 0.4$ $\mu$A/ppm, and requires about 20 seconds to equilibrate fully with the gas sample being monitored; it has a reaction half life of ten seconds.

Microcontroller 80 is used to control the operation of the apparatus. Microcontroller 80 receives signals related to the output signals from carbon dioxide detector 30 and carbon monoxide detector 70, corresponding to the sensed instantaneous carbon dioxide concentration and sensed average carbon monoxide concentration, respectively. These received signals are processed to compute a value corresponding to the end-tidal carbon monoxide concentration in the patient's breath, as described below. The computed value may then be displayed on a display 90, such as a liquid crystal display device.

Preferably, a conventional digital microcontroller system is used having a suitable software-controlled microprocessor, memory, analog to digital conversion, and signal conditioning functions. Of course, as will be apparent to persons of ordinary skill in the art, discrete analog circuit elements and solid state finite state machines also may be used to control the operation of the elements and obtain the concentration measurement.

One suitable digital microcontroller is the model Little Giant LG-X miniature microcontroller, available from Z World Engineering, Davis, Calif. The microcontroller 80 is connected to carbon dioxide detector 30, carbon monoxide detector 70, pump 60, and flow regulator 50 (if one is used) to operate and/or receive signals from those devices. An amplifier interface circuit 82 is used to provide for current to voltage conversion of the signals provided by carbon monoxide detector 70.

Figure 2:
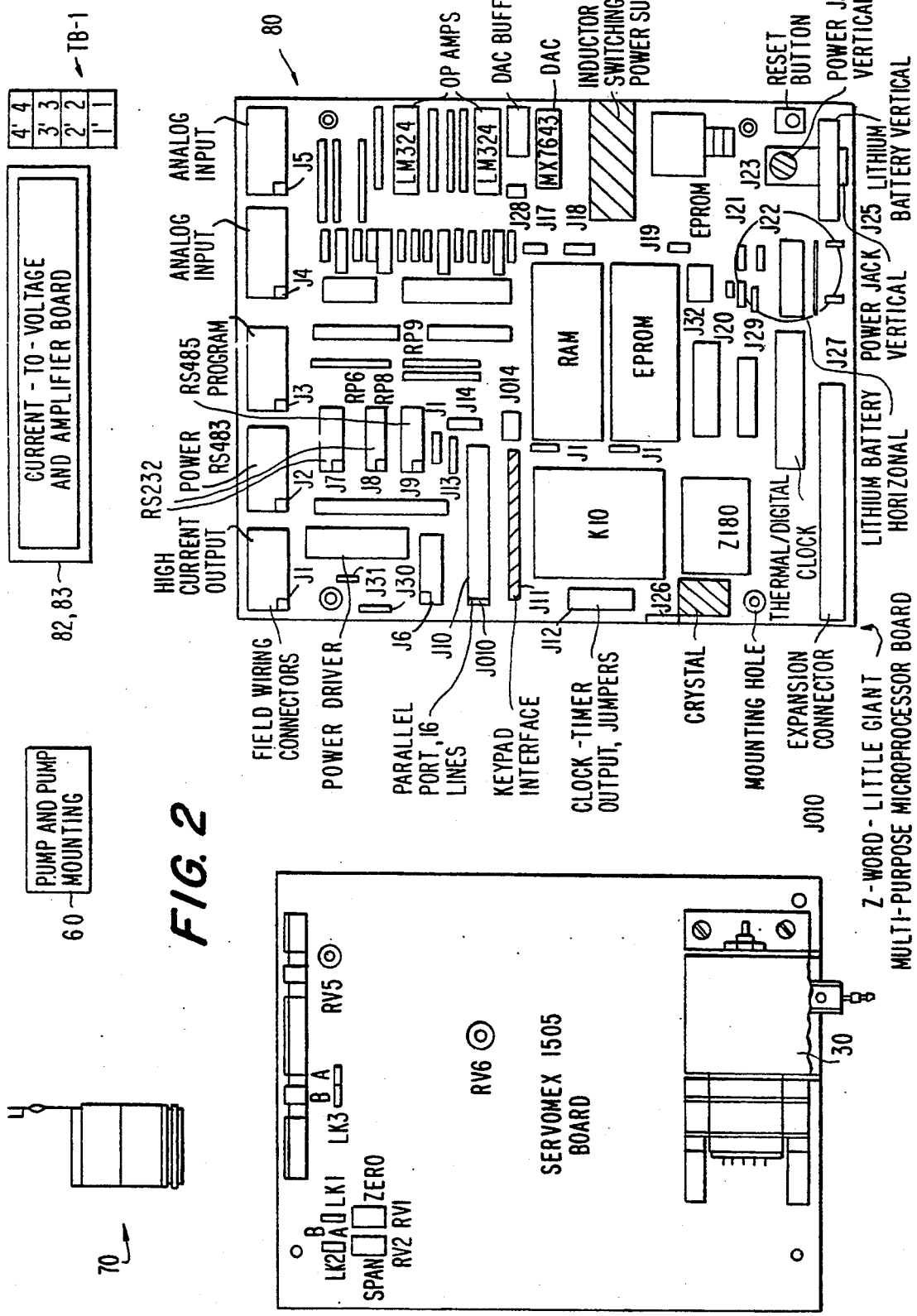
FIG. 2 is a diagram of a multipurpose microcontroller board for controlling the device in FIG. 1.
Figure 2A:
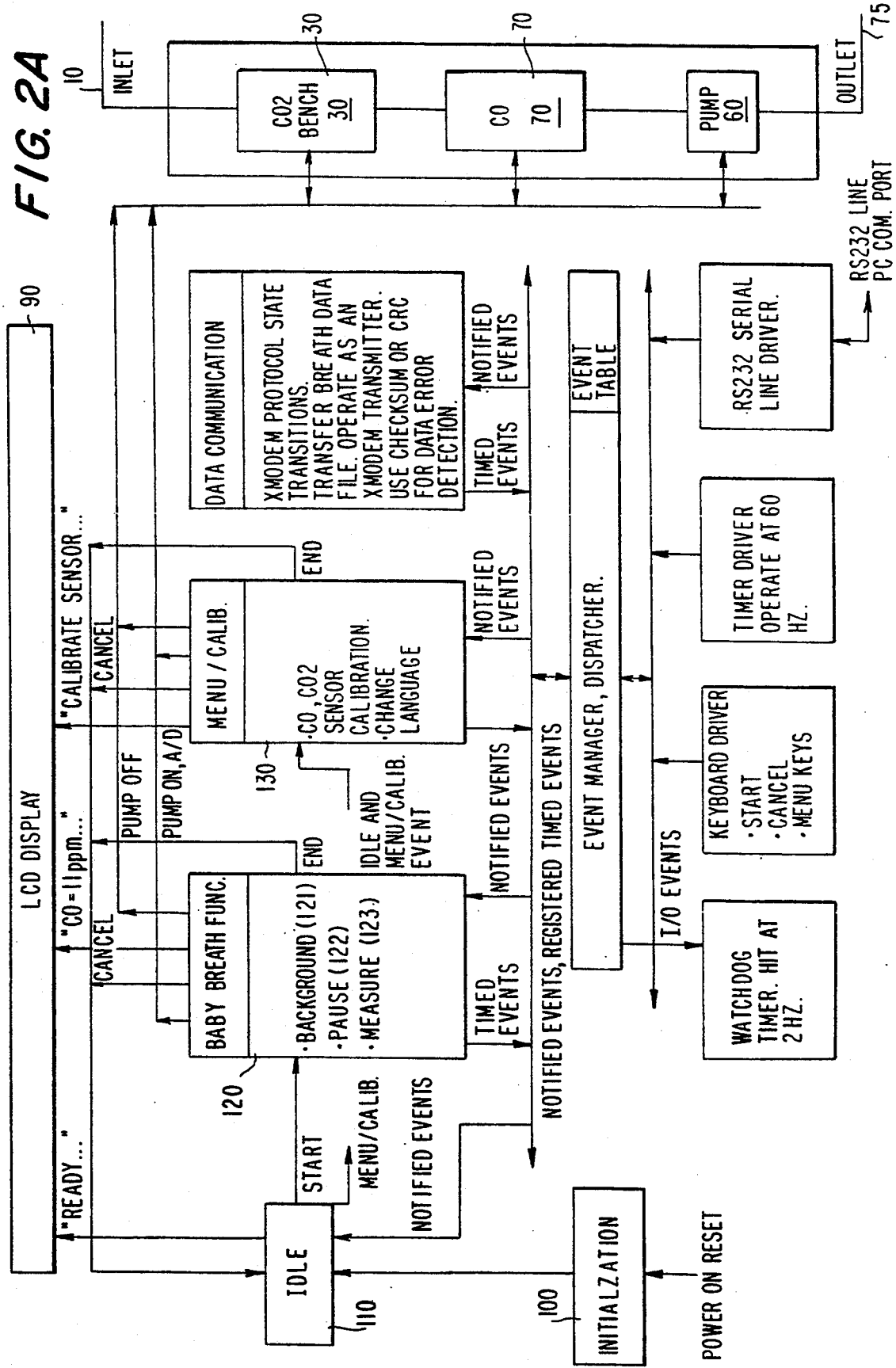
FIGS. 2A-2D are macro flow diagrams for the overall, breath measurements, calibration, and data communication operations of the apparatus of FIG. 1.
Figure 2B:
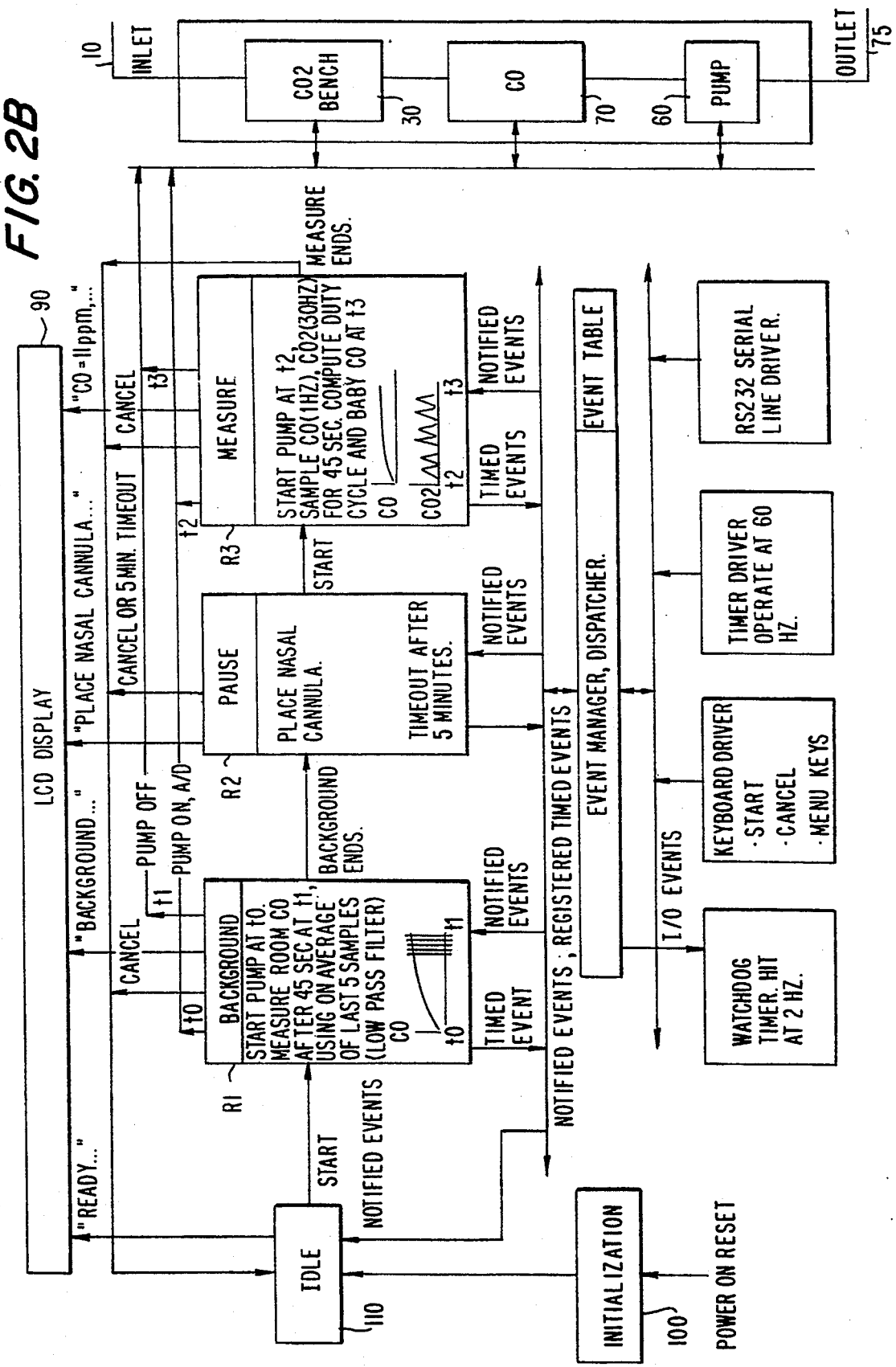
Figure 2C:
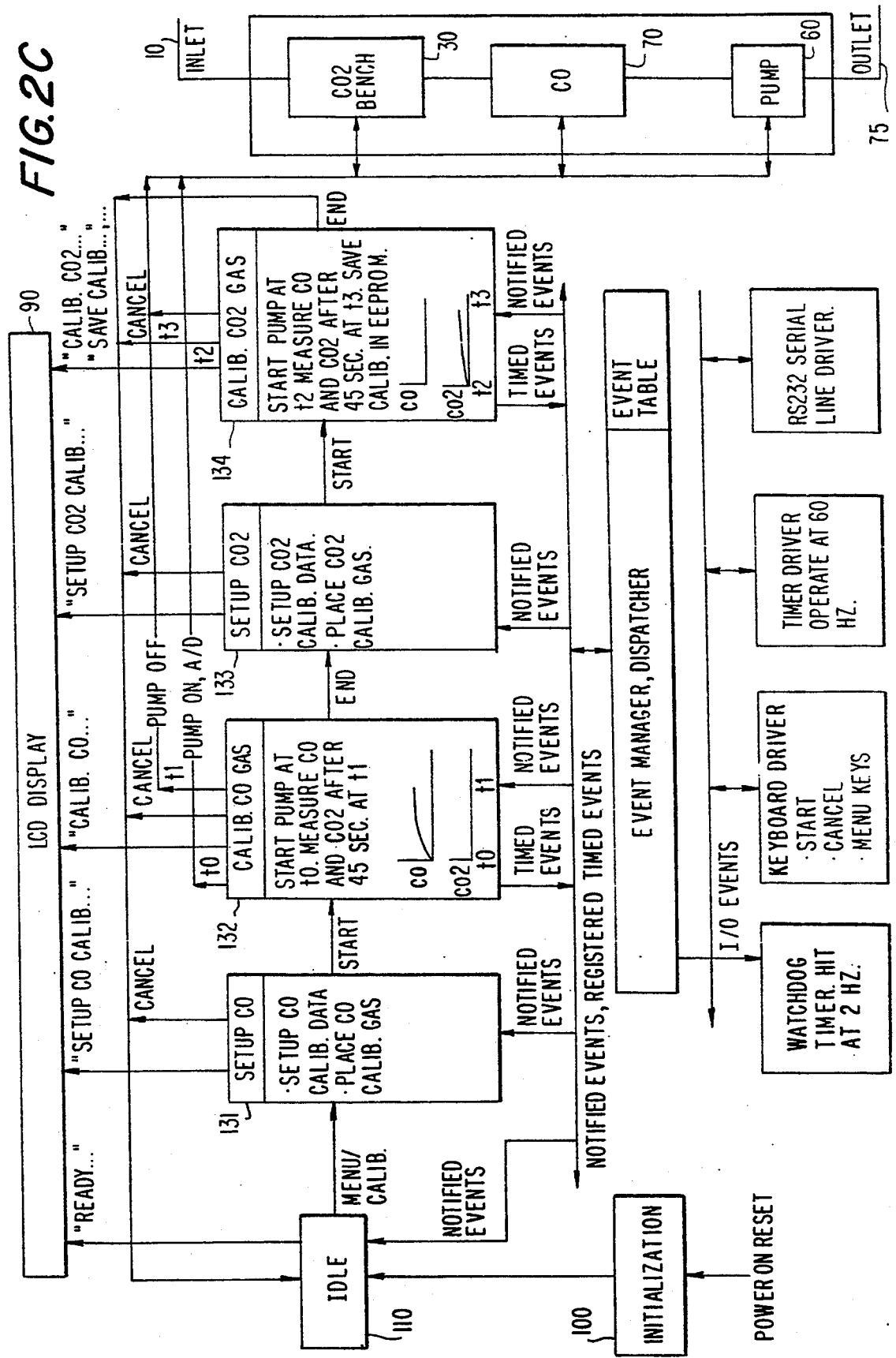
Figure 2D:
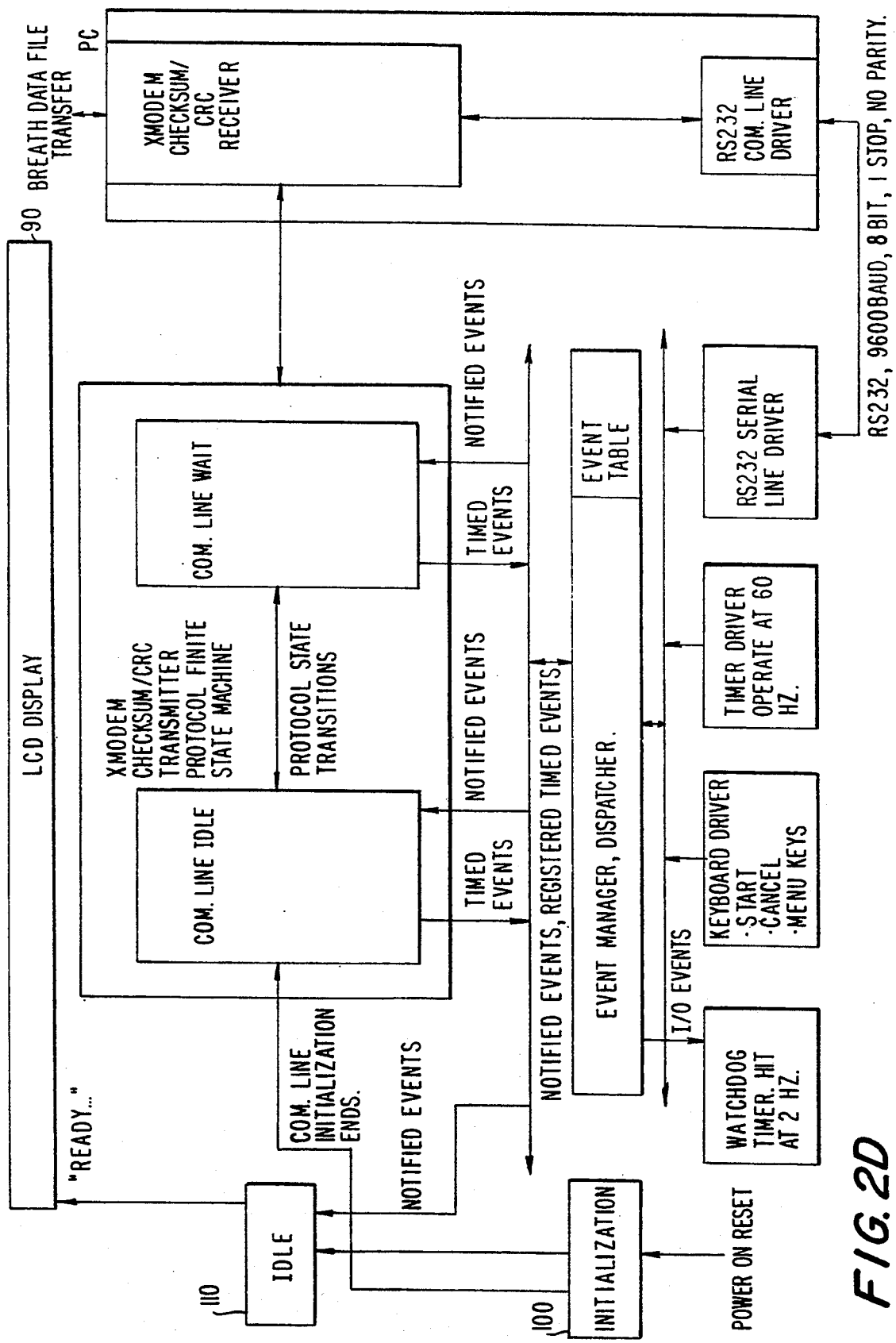
Figure 2E:
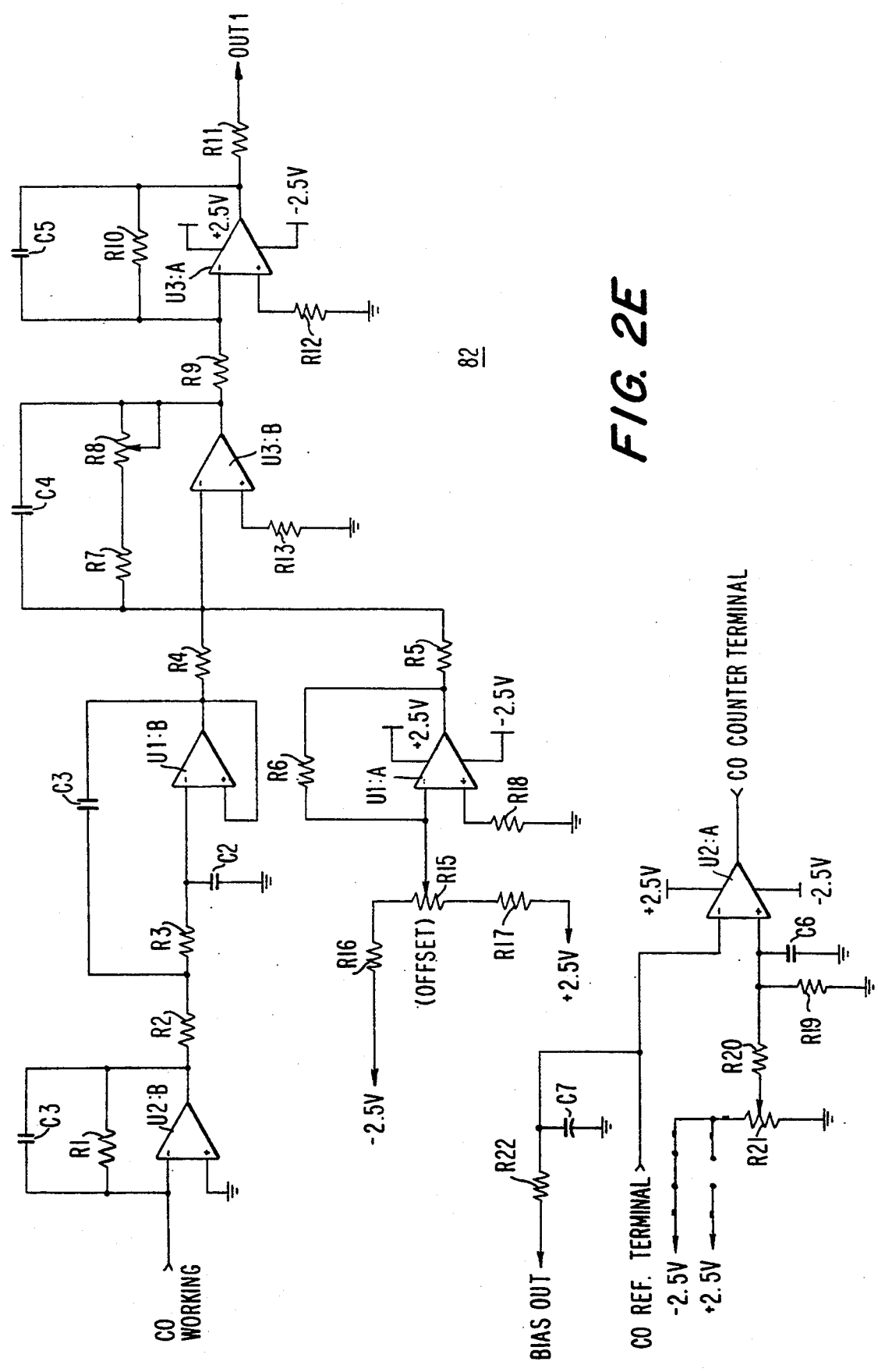
FIGS. 2E and 2F are circuit schematic diagrams for a signal conditioning amplifier and a power supply respectively, for interfacing the carbon monoxide sensor of FIG. 1 and the microcontroller circuit board of FIG. 2.

Referring to FIG. 2E, interface circuit 82 includes three amplifiers, U1B, U2B and U3B, which are preferably OP290 low-noise, dual operational amplifiers available from Precision Monolithics, Inc., Santa Clara, Calif. Amplifier U2B is configured as a current to voltage converter, having a 0.1 $\mu$f capacitor C3 in parallel with a 50k$\Omega$ resistor R1 in the feedback loop. The gain is determined by resistor R1.

Amplifier U1B is a second order lowpass filter with approximately a 0.5 second time constant, using two 470k$\Omega$ resistors R2 and R3 and two 1 $\mu$f capacitors C2 and C3 configured as shown. The filter is used to attenuate electrical noise.

Amplifier U3B is configured as a simple amplifier with gain adjustment potentiometer R8 (100K$\Omega$) in series with a 10k$\Omega$ resistor R7, both of which are in parallel with a 0.1 $\mu$f capacitor C4 in the feedback loop, and a 10k$\Omega$ input resistor R4 at the inverting amplifier input. Potentiometer R8 is used to allow initial calibration to compensate for sensitivity variations in gas detectors. Amplifier U3B also has a secondary input from amplifier U1A, which is configured as an adjustable voltage source that may be used to compensate for a zero gas output of detector 70.

Amplifier U3A is configured as a unity gain buffer designed to isolate the previous stages from any load effects that may be imposed by following circuitry.

Amplifier U2A is configured as shown as an adjustable bias source for the counter electrode of detector 70, as determined by the setting of resistor R21, a 500k$\Omega$ potentiometer. A 10k$\Omega$ resistor R22 provides a means of reading the bias voltage without making direct contact with the gas detector connections. The CO detector amplifier circuit 82 operates as a low power supply voltage to prevent excess leakage currents from imposing undesirable bias currents on the detector 70, and to allow low power continuous biasing of the detector 70 to allow for stable operation. Preferably, amplifiers U2A and U3A also are type OP-290 amplifiers. In the circuits illustrated in FIGS. 2E and 2F, all ground connections are to a virtual ground, which is provided by a CO amplifier power supply circuit 83.

Figure 2F:
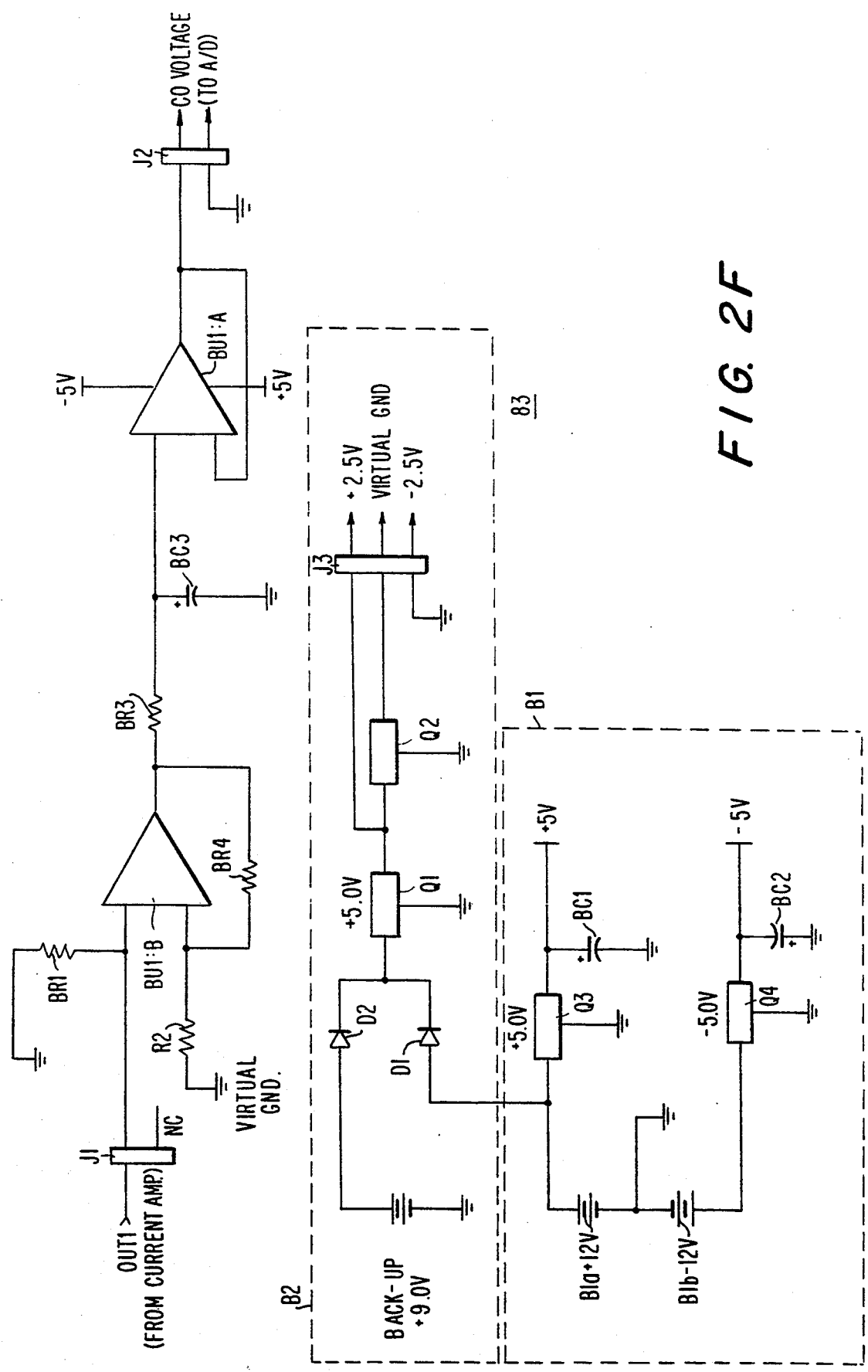

Referring to FIG. 2F, the CO amplifier power supply and interface circuit 83 is shown. The power supply consists of a normal supply B1 and a backup supply B2. Normal supply B1 may be any nominal $+/-12$ volt DC power supply. In one preferred embodiment, normal supply B1 is a regulated power supply derived from AC mains. Alternately, two 12 volt batteries, e.g., rechargeable batteries, could be used.

Devices Q3 and Q4 are integrated circuit regulators (types LM78L05 and LM79L05) which provide $+/-5$ volts respectively, for powering the interface amplifier BU1A. Diodes D1 and D2 (IN4148 type diodes) automatically switch to supply to the CO amplifier BU1A the greater of the normal 12 volt DC supply B1a, and the backup battery B2, an alkaline 9 volt battery.

Device Q1 regulates the supply voltage to $+5$ volts. Device Q2 is an integrated circuit virtual ground supply, model TLE2425, available from Texas Instruments, Dallas, Tex. Its output "splits" the five volt input into a $\pm 2.5$ volt supply with a virtual ground at 2.5 volts DC "real" potential.

Amplifier BU1 of circuit 83 includes two type 1458 dual operational amplifiers, BU1A and BU1B, available from National Semiconductor, Santa Clara, Calif. Amplifier BU1B is configured as a differential amplifier with gain of 1, and has inputs of the virtual ground from the CO amplifier circuit 82 and the CO amplifier circuit 82 output. Resistors BR3 (120k$\Omega$) and capacitor BC3 (10 $\mu$f) provide further low pass filtering with a 1.2 second time constant. Amplifier BU1A is configured as a voltage follower with a low output impedance, for driving the analog input on the Little Giant microcomputer board 80.

Referring to FIG. 2, the Little Giant LG-X microcontroller 80 is programmable using Z-World's Dynamic C language. It uses about 200 mA, contains a microprocessor Z180 having a 9.216 MHz clock frequency and sufficient memory including read only memory ROM, random access memory RAM, and erasable, programmable read only memory EPROM, which collectively contain the software, data, and memory address locations for operating the apparatus, processing the acquired data, and performing the data manipulation and post acquisition processing functions in accordance with the present invention, as described herein. The device also contains counter-timers, including a 2 Hz watchdog timer for automatically resetting the microprocessor in the event of undefined operations or temporary power loss, serial input/output ports, parallel input/output ports, time and date clocks, multichannel analog to digital converter, a digital to analog converter, operational amplifiers for input signal conditioning in single ended or double ended modes, adjustable gain and input voltage ranges, a high current driver output suitable for driving pump 60, and other particular elements provided by the manufacturer which either are used in a conventional manner although not pertinent to the present invention, or are not used. The microcontroller is used in accordance with the manufacturer's directions and specifications, except as otherwise noted, and reference is made to the user manual for the device, entitled "Little Giant Single Board Computer Technical Manual Version E" which is available from the manufacturer, for information regarding configuring and implementing use of the microcontroller.

The display device 90 is capable of providing a display corresponding to the determined carbon monoxide concentration level in the end-tidal breath $CO_{ET}$. Preferably, display 90 includes a display screen for alphanumeric text, including the determined $CO_{ET}$ concentration, and preferably instructions to the operator for operating the device to acquire the appropriate gas samples. Further, display device 90 is preferably user-interactive and includes both a keyboard for operator input and a visual display for prompting the operator to act. Also, the display device 90 may include a paper printer or have an associated printer (not shown) for providing a printed copy of the parameters determined and/or measured, in character text or graphic form. Alternately, or in addition, audible sounds, visual indicators or lights may be used to prompt the operator to perform the appropriate act.

One suitable display device is a model LG-LCD keypad liquid crystal display device, available from Z World Engineering. This device has definable function keys on a keyboard and a visual character display. The visual display includes a 2 line by 16 character LCD. The keyboard has a 4×4 keypad and a beeper for keypad feedback. It is compatible with and directly interfaces with the Little Giant LG-X miniature microcontroller.

Referring to FIG. 2, a printed circuit board layout of the Z World Little Giant microcontroller circuit board is illustrated and the interconnection of elements is described, using the manufacture's conventional pin connections (unless otherwise stated). Referring to terminal board TB1, one or more AC-DC regulated power supplies (not shown) are used to provide the following signals to the four numbered input pins of terminal TB1: −12 volts to pin 1, ground potential to pin 2, +5 volts to pin 3, and +12 volts to pin 4. The corresponding four output pins of terminal board TB1, designated TB1-X' wherein "X" refers to the output pin, are respectively connected in series with the input pins of TB1 and the pins of the apparatus illustrated in FIG. 1 as follows.

Regarding microcontroller 80, the high current output wiring connectors J1 have pin J1-8 connected to the negative terminal of pump 60 for providing a current to drive pump 60 at the selected rate. There are no other connections for wiring connectors J1. The power wiring connectors J2 have pin J2-1 connected to J2-4, pin J2-2 connected to J2-3, pin J2-6 connected to TB1-2' (ground), pin J2-7 connected to TB1-4'(+12 v), and no other J2 pin being connected. The RS485 field wiring connectors J3 are not used in this embodiment.

The analog input field wiring connectors J4 have pins J4-1 and J4-2 connected to amplifier interface board pins J2-1 and J2-2 respectively, pin J4-3 connected to pin PL4-1 on the Servomex 1505 board, and pin J4-4 connected to pin PL4-2 on the Servomex model 1505 board. Analog input pins J5, RS232 port pins J7, and RS485 program pins J9 are not used. The pins at keyboard interface J6 are used to connect a flat ribbon cable to the back panel of the display 90, LCD display device model LG-LCD. The pins J8 for the RS232 port are connected on the back panel to a conventional nine pin D-sub connector. The display 90 interface pins J10 are connected as follows. Pin J10-10 are the common front panel buttons; pin J10-12 is for button #1, pin J10-14 is for button #2, pin J10-16 is for button #3, and pin J10-18 is for button #4.

Regarding the Servomex model 1505 circuit board, it is connected as follows. For device Power, pin PL1-1 is connected to TB1-1' (−12 v), pin PL1-2 is not connected, pin PL1-3 is connected to TB1-2' (ground), pin PL1-4 is connected to TB1-3' (+5 v). For device Thermistor Status, pins PL2 are not connected. For device Nitrous Oxide Compensation, pins PL3-1 and PL3-2 are jumpered and no other pins are connected. For device Signal Output, pins PL4-1 is connected to Little Giant pin J4-3 and pin PL4-2 is connected to Little Giant board J4-4. For device Remote Calibration Adjustment, there are no pin connections.

Figure 7:
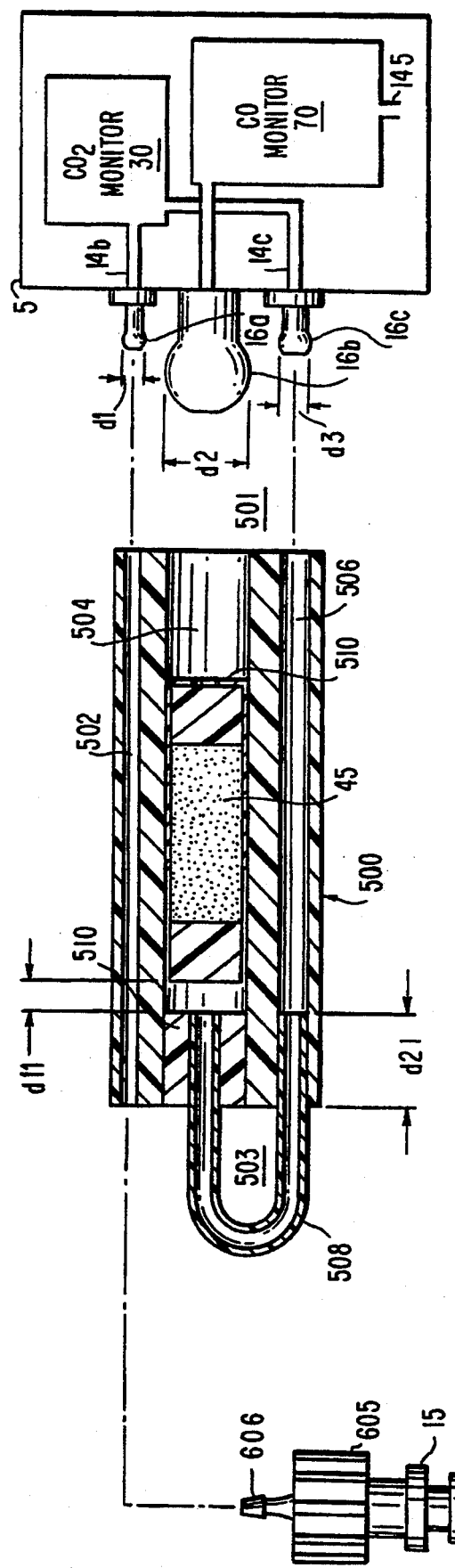
FIG. 7 is a top cross-sectional view taken along line 7—7 of FIG. 5.
Figure 8:
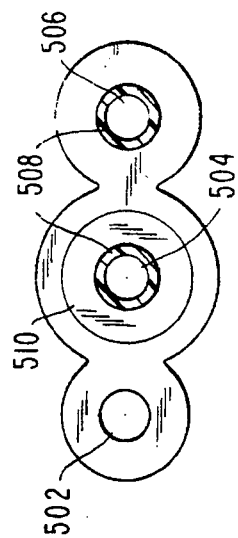
FIG. 8 is an end view taken along line 8—8 of FIG. 5.

Referring now to FIGS. 5–9, in a preferred embodiment of the invention, the segment of tubing between hydrophobic filter 15 and fitting 16a, and the tubing segment between fittings 16b and 16c (the segments illustrated as 14d in FIG. 1) are formed as part of a disposable filter unit 500. Filter unit 500 is preferably constructed as a single housing having three lumens 502, 504, and 506 and a tube segment 508 that is used to connect together lumens 504 and 506 as described in more detail below. Filter unit 500 is preferably made of a soft polyvinyl chloride (PVC), more preferably, a single extruded body having the three lumens that is made of soft PVC. The outer surface of filter unit 500 may have a ribbed surface, for example, longitudinal ribs for a distinctive appearance, horizontal ribs to improve gripping, or both. Preferably, the three lumens are extruded with their longitudinal axes lying in a common plane and with different inner diameters, as illustrated in FIG. 8.

In alternate constructions, filter unit 500 may be formed of three separate extrusions that are glued or otherwise secured together, and the three lumens may be spaced with their respective axes offset vertically and/or horizontally within filter unit 500.

Filter unit 500 has a unit facing end 501, a distal end 503, a plug 510, a cap 512, and filter 45. Filter 45 is inserted into cap 512 and together they are passed into the interior of lumen 504. Filter 45 comprises a length of activated carbon filter 45a and two lengths of cellulose acetate 45b, one on either side of carbon 45a. Carbon 45a may be, for example, a length of activated carbon filter cut from a commercial product known as #R-15243, available from American Filtrona Corp., Richmond Va. USA, which has circumference of about 24.7 mm. Cellulose acetate 46b may be conventional cellulose acetate, such as is used in the manufacture of smoking cigarettes. Carbon filter 45a may have a length of 20 mm. Each piece of cellulose acetate 46b may have a length of 5 mm and circumference of 24 7 mm.

Cap 512 is a cylindrical receptacle made of a material having a low coefficient of friction with respect to the interior wall of lumen 504, e.g., a polyethylene material. It is used to insert filter 45 into lumen 504 without damaging the structural integrity of filter 45 and to form a press fit compressive seal between cap 512, filter 45, and the inside walls of lumen 504. Cap 512 is provided with a thickness on the order of 0.75 mm, and retains filter 45 without distorting its shape. Cap 512 has an open end 513 opening toward the distal end 503 that is about the same diameter as filter 45 for receiving the components of filter 45. Cap 512 also has an aperture 515 facing end 501 that is about the same diameter as the inner or outer diameter of lumen 506. The latter diameter is not critical, except that the end of cap 512 having aperture 515 retain filter 45 as the assembly is inserted into lumen 504 and provide a flow path through filter 45 with an acceptable pressure drop. In this regard, cap 512 is sealingly interposed between filter and lumen 504 so that the analyte flow stream through lumen 504 will pass through filter 45 and inside cap 512 and not around filter 45 or cap 512.

Filter 45 is preferably assembled as a sandwich of acetate 46b, carbon 45a, and acetate 46b, such that at least one acetate section 46b and carbon 46a is inserted into cap 512. The assembled cap 512 and filter 45 is then press-fit inserted into lumen 504 to an appropriate depth. Preferably, filter 45 is finally located to be centered about the midpoint of lumen 504. It is important that an organic lubricant not be used to insert cap 512 into lumen 504. Water may be used as a lubricant, if necessary.

Plug 510 is a cylindrical plug made of PVC that is inserted into lumen 504 on the end 503 side of filter 45. Plug 510 has a length d21 of about 1.0 cm and an air flow passageway 511 extending through its longitudinal axis, having an inner diameter of about 0.3 cm. The length is not critical but must be sufficient to retain tube segment 508. Plug 510 may be secured into lumen 50 by dipping it in a solvent and inserting the dipped part into lumen 504 from end 503 so that they bond together. In a preferred embodiment, when fully seated, cap 512 is spaced from the inner end of plug 510 by a distance d11 of about 0.3 cm. This provides for full access to the entire cross-sectional area of filter 45 by the analyte flow stream.

Tube segment 508 is preferably a length of vinyl tube having longitudinally extending ribs along the inner surface (not shown). The ribs prevent tube 508 from pinching off after it is bent and secured in place in unit 500. In this regard, the ends of tube segment 508 are dipped in solvent and then inserted into lumen 506 and the inner passageway 511 of plug 510 to a depth sufficient to retain tube 508 securely. A suitable depth is about 1.0 cm. Accordingly, tube 508 may have an overall length of about 6 cm. an outer diameter of about 0.3 cm., and an inner diameter of about 0.15 cm. Alternately, tube 508 may be frictionally fit into lumen 506 and passageway 511.

In a preferred embodiment, lumen 502 has an inner diameter of about 0.15 cm., lumen 504 has an inner diameter of about 0.83 cm., and lumen 506 has an inner diameter of about 0.3 cm., connector 16a has a maximum outer diameter d1 of about 0.19 cm., connector 16b has a maximum outer diameter d2 of about 0.87 cm., and connector 16c has a maximum outer diameter d3 of about 0.34 cm. The thickness of each lumen wall may be on the order of 0.15 cm., such that there is about a double thickness between adjacent lumens in the midplane of unit 500, as illustrated in FIG. 7. By using these dimensions, which are exemplary and not critical, the different lumen diameters may be frictionally fit securely only onto the correspondingly sized bulkhead connectors 16a, 16b, and 16c (see FIG. 7). This assures that filter unit 500 will be correctly connected to monitor 5. Alternate spacing or orientation of the three lumens and the corresponding bulkhead connectors could be used to accomplish the same function. Also, the bulkhead connectors could be recessed so that filter 500 is supported by both the recess and the connectors.

Figure 9:
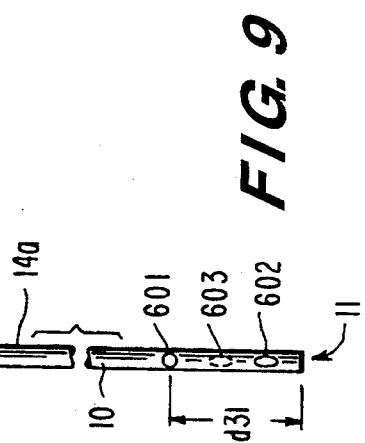
FIG. 9 is a top view of an alternate embodiment of a nasal canula of FIG. 1.

Referring to FIGS. 6 and 9, a preferred embodiment of the invention employs obtaining a gas sample using canula 10, a fitting 605, and hydrophobic filter 15. Fitting 605 is preferably a male tapered luer with an integral locking ring and a barb 606 for a 1/16" (0.159 cm.) inner diameter tube. It is designed to pass into lumen 502 of filter unit 500 and remain securely connected by a frictional fit. Fitting 605 may be made of nylon, preferably a white nylon. One such suitable fitting is part no. MTLL210-1, available from Value Plastics, Inc., Fort Collins, Colo., USA.

Filter 15 may be a part No. 3.0 mm. filter F1#57120, available from Filtertek, Hebron, Ill., USA, which screws directly into the patient side of fitting 605.

Canula 10 is preferably a length of plastic tube such as an infant feeding tube with a distal tip that has been modified to provide an insertion mark 601 and two apertures 602 and 603, all located within a distance d31 of about one centimeter of end 11. End 11 is preferably open. Canula 10 also has a tapered receptacle 610 which is configured to mate securely with a tapered protrusion 15' (See FIG. 6) of filter 15 in a conventional manner.

Insertion mark 601 provides a depth gauge for the user to insert end 11 into the patient's nostril, e.g., until insertion mark 601 enters the nostril. Apertures 602 and 603 are spaced equidistantly between mark 601 and end 11 and located on opposite sides of the tubing. Apertures 602 and 603 extend only through one side of tube 10. More or different apertures and different aperture locations also may be used. One suitable tube is model No. 1219-15 5FRx36" feeding tube, available from Medovations, Inc. Milwaukee, Wis., USA, which is customized as noted, and which mates directly to the tapered protrusion of filter 15.

Preferably, canula 10 is separately packed in a sterile package which is opened immediately prior to use. In this regard, filter 15 and fitting 605 may be provided together with canula 10 in sterile packaging, separate from canula 10 and filter unit 500 in clean packaging, or together with filter unit 500 (and optionally completely or partially preassembled therewith) in clean packaging. If desired, the complete canula 10, filter 15 and filter unit 500 could be preassembled and packed in sterile packaging.

According to a preferred embodiment of the present invention, the end-tidal carbon monoxide concentration of the patient is measured in the following manner. An initial value of carbon monoxide may be obtained for analysis purposes. Pump 60 is then started and a sample of room air is drawn through monitor 5 at the selected flow rate of, e g., 50 ml/min, past the carbon dioxide detector 30 and the carbon monoxide detector 70. At the end of a first time period, e.g., 45 seconds, the measures of the concentrations of the carbon dioxide and carbon monoxide in the sample cells of the carbon dioxide sensor 30 and carbon monoxide sensor 70 are obtained, respectively. The measures are obtained as analog signals from the detectors 70 and 30, e.g., sensed currents converted to conditioned voltages $v_{co}$ and $v_{co2}$, which are respectively digitized into n-bit words (n is preferably 8) at selected sampling rates and passed into a data buffer and/or memory. The values are stored as $CO_{room}$ and $CO_{2zero}$.

Pump 60 is then turned off and the cannula 10 is placed in the patient's nostril, preferably in the posterior nasal pharynx. Then the pump 60 is turned on again and an analyte stream of breath is drawn past the respective gas detectors 70 and 30. The concentrations of carbon monoxide and carbon dioxide are respectively sensed and sampled during a second time period, e.g., 45 seconds.

The acquired measures of the carbon dioxide concentration over the second time period are evaluated. First, the relative changes in the carbon dioxide concentration are evaluated to determine the duty cycle corresponding to the end-tidal portion of the patient's breath. An average of the end-tidal $CO_2$ concentration ("$CO_{2ET}$") to the average $CO_2$ is obtained, providing the duty cycle dc.

The end tidal CO concentration ("$CO_{ET}$") is then determined from the following relationship:

$$CO_{ET} = [CO_{mean} - CO_{room}]/dc \qquad (1)$$

where $CO_{mean}$ is the average or mean carbon monoxide concentration at the end of the second period, and dc is the duty cycle determined for $CO_{2ET}$.

Referring to FIG. 1, the macro flow diagrams of FIGS. 2A to 2D, a preferred embodiment of the operation of the present invention is now described. In this embodiment, display device 90 is configured to use four buttons which are used for-controlling the operation of the apparatus. Button #1 is a start button to initiate some action by the apparatus to reset the apparatus operation, button #2 is a reset button, button #3 is a select button to select some option from a menu, and button #4 is a menu button to display one or more instruction and/or operation menu. Each button is activated by pressing in and then releasing the button. Other alternatives for providing user input in an interactive device may, of course, be used.

Referring to FIG. 2A, the device becomes activated on power on or reset (pressing button #2) and enters an initialization sequence at step 100. During initialization, the operating code of microcontroller 80 is booted and various system checks and device initializations are performed. Following initialization, the routine passes to an idle state at step 110, where it waits for user input. During the idle state, the system preferably generates a suitable message on display 90, e.g., "Ready, press 1 to start". Thus, during the idle step 110, the user may provide an input by pressing button #1 to start a measuring sequence. This passes the operating routine to step 120.

Also during the idle state 110, the operator may press button #3 to select a sequence from a menu displayed on the display unit 90, and button #4 to display various operation sequences. One such sequence is a calibration routine for calibrating the carbon monoxide detector 70 and carbon dioxide detector 30 at step 130. The operator also may press button #2 at any time to exit whatever routine it is executing, reset the apparatus, and return the routine to step 100.

Referring to FIGS. 2A and 2B, in response to pressing button #1 in the idle state 110, the routine moves from the idle step 110 to step 120 for the sequence for determining end-tidal carbon monoxide concentration $CO_{ET}$. There are three phases to this determination, a sequence at step 121 for measuring the background carbon monoxide $CO_{room}$ during a first time period, a pause or delay period at step 122, and a sequence at step 123 for measuring breath carbon dioxide $CO_2$ and carbon monoxide CO during a second time period.

In the present invention, before each sample is obtained, pump 60 is off for a delay time period. This allows the CO detector to return to a zero state so that effectively no CO is in the sample cell. When desired, a supply of inert gas may be provided and pump 60 activated for a time to clear the sample cell of any CO (and $CO_2$) gas. A three-way valve and an actuator may be included (not shown) to achieve this cell clearing function. The delay time period is at least about one minute, more preferably three minutes.

In the background measurement sequence step 121, the user is prompted to place the end 11 of cannula 10 somewhere in the vicinity of the patient, but not inside the nostril and then to press button #1. In response to pressing button #1, pump 60 is activated at time to and the background room air is drawn through tubing 14 and during a first time period of approximately 45 seconds. During this time, display 90 preferably displays a suitable message corresponding to the duration of the background measuring test, e.g., how much time remains to complete the test, in seconds or in percent.

At time $t_1$ at the end of the first time period, pump 60 is turned off. The carbon monoxide concentration in the sample cell of the carbon monoxide detector 70 is then determined and recorded in memory as $CO_{room}$. As noted, the carbon monoxide gas detector has a time response to the analyte flow that produces an average carbon monoxide concentration. The digitized samples corresponding to the carbon monoxide concentration are then processed so that the output signal is the average of the last five acquired samples. Preferably the determined concentration value is displayed, e.g., in parts per million (ppm). The amplitude of the voltage signal $v_{co}$ corresponding to the averaged sensed carbon monoxide concentration $CO_{room}$ from detector 70 that is displayed, also may be displayed for diagnostic purposes.

The CO and $CO_2$ gas equations used to convert the sampled voltage signals corresponding to the detector signal outputs to gas concentrations are:

$$CO\ ppm = m_1 v_{co} + c_1 \qquad (2)$$

$$CO_2\% = m_2 v_{co2} + c_2, \qquad (3)$$

where $m_1$ and $c_1$ are the slope and intercept calibration constants relating the voltage $v_{co}$ derived from the CO detector 70 output in response to the concentration of carbon monoxide in a sample to ppm, and $m_2$ and $c_2$ are the slope and intercept calibration constants relating the voltage $v_{co2}$ derived from the $CO_2$ detector 30 output in response to the carbon dioxide concentration in a sample, in percent.

Thus, at time $t_0$, with CO=0 ppm, using the above equation:

$$0 = m_1 v_{co} + c_1 \text{ and} \qquad (2.1)$$

$$c_1 = -m_1 v_{co\text{-}0} \qquad (2.2)$$

where $v_{co\text{-}0}$ corresponds to the signal produced by CO detector 70 at time $t_0$. At time $t_1$, $$CO_{room}\,ppm = m_1\,v_{CO-1} + c_1. \quad (2.3)$$
$$= m_1\,v_{CO-1} - m_1\,v_{CO-0} \quad (2.4)$$
$$= m_1\,(v_{CO-1} - v_{CO-0}) \quad (2.5)$$

where $v_{co\text{-}1}$ corresponds to the signal produced by CO detector 70 at time $t_1$.

When pump 60 is stopped at time $t_1$ at the conclusion of the background step 121, the CO is measured and the routine enters pause step 122. During the pause step 122, the operator is prompted to place the nasal cannula 10 inside the patient's nostril and then to press button #1 to resume the measurement sequence. The system preferably displays a suitable message on display 90, e.g., "place nasal cannula", to prompt the user to place the cannula 10. The pause step 122 preferably includes a minimum delay period Timeout of about ten seconds and a maximum delay period Timeout of about five minutes. Thus, if the operator does not press the start button #1 within the Timeout period, the system will return to the idle state 110. The Timeout period is used to provide for sampling the room air and patient carbon monoxide concentrations within a time period wherein it is not likely that the room air concentration level will change very much. The Timeout period also is selected to permit the operator sufficient time to insert the nasal cannula 10 in a patient, such as a newborn infant, which may require some time to accomplish.

Once the cannula 10 is place, the operator presses button #1 to resume the measurement sequence 123. At time $t_2$, pump 60 is turned on for a second time period, which is preferably the same as the first time period, i.e., 45 seconds. Initial CO and $CO_2$ samples may be obtained for analytical purposes. During this second time period, the display 90 preferably displays a suitable message corresponding to the duration of the measuring test, e.g., how much time remains to complete the test, in seconds or in percents. At time $t_3$, at the end of the second time period, pump 60 is turned off.

During the second time period, the signals corresponding to the $CO_2$ concentration obtained from $CO_2$ detector 30 are acquired. The relative changes in $CO_2$ concentration over time are then used to calculate the duty cycle dc of the patient's end-tidal breath. Preferably, the signal corresponding to the carbon dioxide concentration is periodically sampled, e.g., the analog signal is digitized at a first sampling rate, e.g., 30 Hz during the second time period. These samples are stored in a data buffer for post data acquisition processing and analysis.

Also, the signals corresponding to the CO concentrations obtained from detector 70 are acquired during the second time period. Preferably, the carbon monoxide concentration is periodically sampled, e.g., the analog signal is digitized at a sampling rate of 1.0 Hz during the second time period. These samples also are stored in the data buffer for analysis.

Figure 3A:
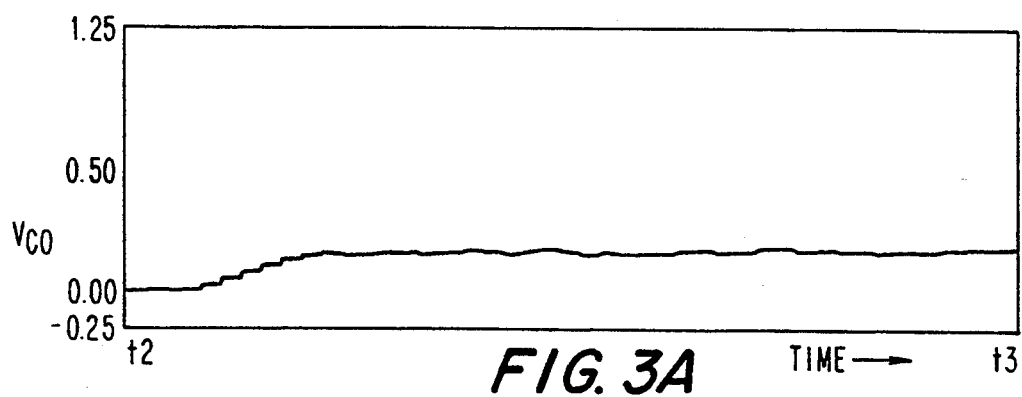
FIGS. 3A and 3B are graphical illustrations of measurements of carbon monoxide and carbon dioxide concentrations acquired using the device of FIG. 1.
Figure 3B:
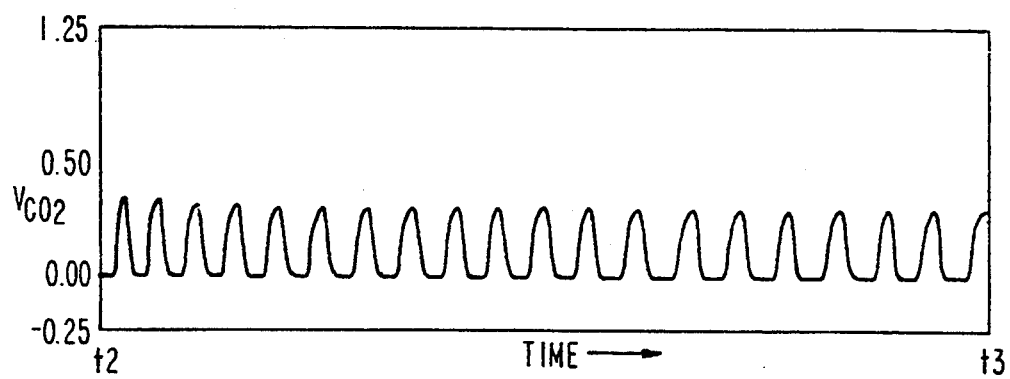

FIGS. 3a and 3b illustrate representative sampled waveforms of the signals $v_{co}$ and $v_{co2}$ provided by the CO and $CO_2$ detectors 70 and 30 respectively, during a second time period. The waveforms thus display the concentration levels sensed corresponding to the calibrated CO and $CO_2$ levels. In these representative drawings, the calibration functions were:

$$CO\,ppm = 12.11\,v_{co} + 0.95;\text{ and}$$

$$CO_2\% = 11.96\,v_{co2} + 0.$$

The calculated duty cycle dc was 42.30%, the $CO_{ET}$ was 2.10 ppm, the $CO_{room}$ was 2.01 ppm, the $v_{co\text{-}0}$ was $-0.78$ v and the $v_{co\text{-}1}$ was 0.088 v. The $v_{co}$ min was $-0.05$ v and the $v_{co}$ max was 0.17 v (corresponding also to the start (t2) and stop (t3) measurement voltages). The maximum $v_{co2}$ was about 0.42 volts.

The 30 Hz sampling rate of $CO_2$ was selected because it corresponds to the anatomical waveform of respiration from which the ratio of the end-tidal portion total air can be derived. The $CO_2$ sensor time response of 120 ms gives adequate resolution without acquiring excessive data. The sampling rate of 1 Hz for the CO detector voltage $V_{co}$ was selected because the CO detector has a much slower response time (the half time of the CO response is about ten seconds) which cannot discriminate the end-tidal portions and room air. Sampling at a higher rate would not significantly improve the data resolution. The selected rates were selected as compromises between collecting sufficient data with adequate resolution in view of the sensor response time, and may be changed according to the sensors used and the particular conditions of use.

Following acquisition of the data, the data is processed by the microprocessor Z180 of microcontroller 80 to derive the duty cycle and the end-tidal CO concentration $CO_{ET}$. The digitized samples of the voltage $v_{co}$ are passed through a low pass digital filter, which may be implemented by suitable software, which takes an average of the last five samples. This filter is used to suppress noise. It also advantageously permits use of the output of the digital filter without further averaging or storage of separate values. The corresponding average or mean CO concentration at time $t_3$, $CO_{mean}$, is thus $$CO_{mean} = m_1\,V_m + c_1. \quad (4)$$

where $V_m$ is the average of the last five voltage samples $v_{co}$.

The duty cycle dc is calculated based on analysis of the sampled voltages $v_{co2}$ between time $t_2$ and $t_3$, as follows:

$$dc = \frac{[\text{the number of }CO_2\text{ samples} > V_t]}{[\text{total number of }CO_2\text{ samples}]}$$
$$= \frac{[\text{the number of }CO_2\text{ samples} > 1.5\%]}{[\text{total number of }CO_2\text{ samples}]}$$

where $V_t$ is a selected threshold voltage corresponding to, e.g., a 1.5% $CO_2$ concentration, and is obtained from the $CO_2$ gas equation (3) as follows:

$$1.5\% = m_2\,V_t + c_2,$$

$$V_t = (1.5 - c_2)/m_2.$$

For an ideal $CO_2$ detector 70, $m_2 = 10$ and $c_2 = 0$, such that $V_t = 0.15$ volts. Of course, other values and threshold voltages could be used as appropriate in the particular circumstances.

Then, the patient's end-tidal CO concentration $CO_{ET}$ is:

$$CO_{ET} = (CO_{mean} - CO_{room})/dc. \quad (1)$$

This may be calculated in a straightforward manner from the acquired data.

Figure 4A:
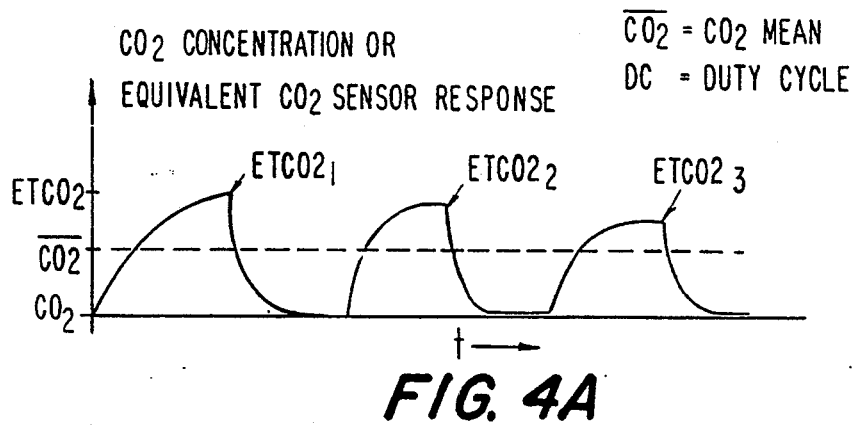
FIGS. 4A and 4B are graphical illustrations of the carbon monoxide and carbon dioxide concentrations in a representative breath flow.
Figure 4B:
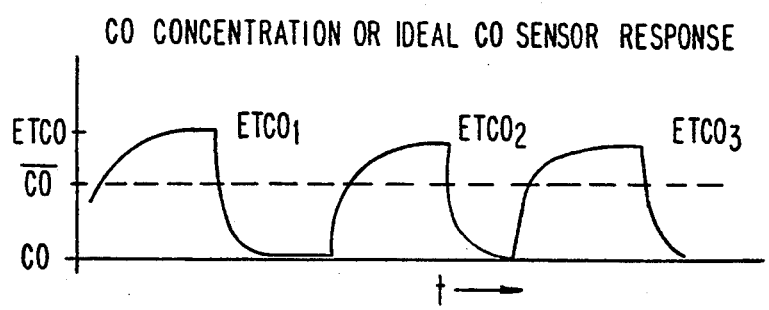

The foregoing equations are based on the realization that the physical behavior of CO and $CO_2$ are very similar with respect to, for example, diffusion, flow rates and other behavior characteristics in the patient's cardiopulmonary system. Accordingly, it can be assumed that ratio of the end-tidal $CO_2$ to the total $CO_2$ is the same as the ratio of the end-tidal CO to the total CO. This is illustrated in FIGS. 4a and 4B. Further, it can be assumed that the $CO_2$ concentration of room air is approximately 0 and that the end-tidal $CO_2$ concentration is related to the duty cycle of the breath waveform and the mean value of the $CO_2$ concentration, namely:

$$CO_{2ET} * dc = CO_{2mean}. \quad (5)$$

Thus, based on these assumptions, the CO and $CO_2$ ratios are $$\frac{CO_{2ET} - CO_{2room}}{CO_{2mean} - CO_{2room}} = \frac{CO_{2mean}/dc - 0}{CO_{2mean} - 0} = \frac{CO_{ET} - CO_{room}}{CO_{mean} - CO_{room}}$$

and thus $$1/dc = \frac{CO_{et} - CO_{room}}{CO_{mean} - CO_{room}} \quad (6)$$

and the total end-tidal $CO_{ET}$ is $$CO_{ET} = \frac{(CO_{mean} - CO_{room})}{dc} + CO_{room} \quad (7)$$

Therefore, to obtain the patient's actual end-tidal CO level produced, the portion of the patient's breath from the $CO_{room}$ concentration (i.e., the CO level that was inhaled by the patient) must be subtracted from the total, which yields the equation (1) above.

The determined values are then displayed on display 90 and any desired printouts of the acquired data may be made or stored to a memory device or medium for subsequent analysis, as desired. The routine then exits the measuring sequence 120 and returns to the idle state at 110. The display preferably include the determined $CO_{ET}$, e.g., in ppm, and also may provide the duty cycle of the carbon dioxide waveform corresponding to the end-tidal portion, and/or various voltages from the detectors 30 and 70, such as minimum and maximum voltages corresponding to CO and $CO_2$, and initial and final voltages for $CO_{mean}$ and/or $CO_2$ during the second time period. It is noted that, in connection with the second time period for monitoring the patient's breathing, the time references $t_o$ and $t_1$ may be used in place of time references $t_2$ and $t_3$ respectively.

Preferably, the data from the measurement cycle just finished will remain displayed for a period of time to allow the operator to record manually the data. The display 90 may be cleared by pressing button #1 (or reset #2). Following measurement of a sample, the aforementioned delay time period of about one minute (or three minutes) is provided to allow the CO and $CO_2$ detectors 70 and 30 to decay to a "zero" state before the next background measurement cycle begins. Preferably, any attempt to obtain another measurement before the end of the delay period will be simply delayed until the expiration of that time, and then automatically commence.

Referring to FIGS. 2A and 2C, the CO and $CO_2$ detectors 70 and 30 are periodically calibrated using conventional CO and $CO_2$ gases having known concentrations. To begin the calibration sequence 130, the system must be in the idle state 110. The operator then presses button #4 to call the menu up on display 90. The menu will display an appropriate message such as "menu 1. Calibrate CO/CO2 sensor. Activate button #1 to start". The operator then presses button #1 which begins the calibration sequence 130. The calibration sequence involves the selection of test gases of known concentrations, inputting the known concentration values into the system during set-up sequence 131 for CO and setup sequence 133 for $CO_2$, operating the pump 60 to draw the known gas into the system and determining the signal level produced by the detector (30 or 70 depending on the gas; only one detector is calibrated at a time) in response to the known gas concentration during measurement sequence 132 for CO and measurement sequence 134 for $CO_2$.

In a preferred embodiment, the display 90 is used to provide a sequence of instructions for the operator to input data, such as which gas detector is to be calibrated and the concentration of the test gas that is to be used (sequences 131 and 133). This is followed by providing a sample of that test gas, which is then sampled and measured (sequences 132 and 134). Preferably, at least two gas samples at different known concentrations are used for each of CO and $CO_2$. From these two samples, the foregoing gas calibration equations (2) and (3) for converting a provided voltage to a gas concentration are determined. The calibration equations are reasonably accurate over the concentration ranges of interest, e.g., accurate within 10%.

In one embodiment, in sequences 131 and 133, a keyboard associated with display 90 may be used to input the test gas type and concentration data directly by pressing alphanumeric characters. In accordance with a preferred embodiment using the Little Giant LCD display device, select button #3 is used to toggle a digit that is underscored on the display screen menu between values, to display the known gas concentration value. The menu button #4 is used to move the underscore along the displayed characters for selecting the character to be changed. Start button #1 is used to indicate that the character now displayed is the correct value, which value is then stored for use in deriving the calibration function for the gas detector being calibrated. The calibration is thus conducted in a known manner and preferably produces a linearized calibration function.

Preferably two samples of each gas at known concentrations are used. Thus, two points are obtained, (v1, p1) and (v2, p2), where v1 and v2 are the measured voltages and p1 and p2 are the corresponding known gas concentrations. Using these two test points, the calibration constants are conventionally obtained as follows:

$$m = (p2-p1)/(v2-v1) \quad (8)$$

$$c = (p1\ v1 - p2\ v1)/(v2-v1). \quad (9)$$

Referring to FIG. 2D, a macro flow diagram of the data communication function of the apparatus is shown. Initialization step 100 provides for initialization of the communications channel. This channel establishes serial RS232 communication under the industry standard x-modem protocol with external devices, such as portable computers. It is used to monitor the operation of the gas analyzer and for development and diagnosis of system failures. Any terminal device such as a portable computer equipped with a suitable communication program such as BITCOM, or PROCOMM, will automatically be able to receive the data files at 9600 baud for the examination and evaluation.

The foregoing routines may be implemented in software for controlling the described elements in a conventional manner that is within the abilities of a person of ordinary skill in the art, as set forth in the copending and commonly assigned application Ser. No. 07/899,261, the disclosure of which is incorporated herein by reference. Implementation of the present invention in alternate microprocessor controlled devices, analog circuit controlled devices, and finite state machines with appropriate controlling software, integrated and/or discrete circuit elements and logic circuits, is believed to be within the ability of a person of ordinary skill in the art.

One advantage of the present invention that it provides a simple and easy-to-use device that accurately and relatively quickly obtains a measure of the end-tidal carbon monoxide concentration of a patient. The determination is made immediately following acquisition of the breath sample and is thus performed in real-time. It overcomes the above-noted problems of the prior art techniques. Another advantage of the invention is that it provides a reusable apparatus with a disposable canula and a disposable filter unit containing a consumable organic filtration medium. This facilitates quick and easy replacement of parts requiring replacement due to the end of their useful life while maintaining the durable measuring apparatus intact. The disposable filter unit is particularly advantageous because it incorporates conventional materials processing which can be performed in high volume production runs at low cost, and uses simple, inexpensive assembly procedures, rather than more complicated fabrication techniques, to obtain very low-cost units. Similarly, the use of off-the-shelf fittings and hydrophobic filters provides additional cost savings over proprietary products. The present invention is particularly useful for detecting abnormal levels of hemolysis in newborn and premature infants, as well as determining incipient hyperbilirubinemia, elevated levels of bilirubin, the likelihood of the onset of jaundice, and the resolution of those conditions over time. Importantly, with respect to newborn and premature newborns, it provides for enhanced detection of potential problems before the newborns are discharged from the hospital.

One skilled in the art will appreciate that the present invention can be practiced by other than the described embodiments, which are presented for purposes of illustration and not of limitation.

We claim:

1. A method of filtering a gas sample for use with a non-invasive end-tidal gas flow monitor containing a first sensor for detecting the amount of a first gas component in a gas sample, a second sensor for detecting the amount of a second gas component in the gas sample, a first connector in communication with the first sensor, a second connector in communication with the first sensor, a third connector in communication with the second sensor, comprising:

providing a body having a first end and a second end and first, second, and third lumens extending through the body between the first and second ends;

providing a first consumable filtration medium for removing selected undesired components from the gas sample;

locating the first consumable filtration medium in one of the second and third lumens;

connecting the second and third lumens with a tube segment at one of the first and second ends, thereby providing the first lumen as a first gas flow path between the first and second ends of the body and providing the interconnected second lumen, tube segment, and third lumen as a second gas flow path through the body; and passing said sample of gas through said first consumable filtration medium.

2. The method of claim 1 further comprising forming the body as an extruded tri-lumen body having simultaneously coextruded first, second, and third lumens.

3. The method of claim 2 wherein forming the body further comprises providing the first, second, and third lumens with walls of about the same thickness.

4. The method of claim 2 wherein forming the body further comprises co-extruding the first, second, and third lumens with respective first, second, and third longitudinal axes in a common plane.

5. The method of claim 1 wherein providing the body further comprises providing the first, second, and third lumens with different inner dimensions.

6. The method of claim 5 further comprising inserting a plug in one of the second and third lumens at the one end receiving the tube segment, and providing an interior flow passageway through the plug having an inner dimension that corresponds to the inner dimension of the other of the second and third lumens, wherein the inserting step further comprises inserting the tube segment into the plug flow passageway and the other lumen.

7. The method of claim 6 further comprising providing said first, second, and third lumens and said plug with a generally circular cross section.

8. The method of claim 7 wherein providing the body further comprises forming the body as an extruded or molded tri-lumen tube.

9. The method of claim 7 wherein inserting the tube segment further comprises bonding the tube segment to the plug flow passageway and the other of the second and third lumens.

10. The method of claim 5 further comprising providing the lumens with longitudinal axes in a common plane.

11. The method of claim 5 further comprising forming the first, second, and third lumens with dimensions for interconnecting to the first, second and third connectors to form a secure frictional engagement.

12. The method of claim 1 wherein providing the first filtration medium further comprises:

providing a first length of cellulose acetate;

providing a second length of cellulose acetate;

providing a length of activated carbon having an outer circumference; and positioning the length of activated carbon between the first and second lengths of cellulose acetate.

13. The method of claim 12 further comprising sealingly interposing a thin cap between the outer circumference of the activated carbon and an interior wall of the second gas flow path, and providing the cap with an aperture at each end of the carbon for providing a gas flow path therethrough.

14. The method of claim 1 further comprising:
providing a fitting having a barbed end for connecting to one end of the first lumen;
providing a hydrophobic filter; and
connecting the hydrophobic filter to the fitting.

15. The method of claim 14 further comprising providing a canula having a first end and a second end, the first end having a first and second aperture for receiving said sample of gas from the patient and marking the canula with an insertion mark at a distance from the first end on the order of 1.0 centimeter, and connecting the second end to the hydrophobic filter.

16. The apparatus of claim 14 wherein the passing step further comprises passing said gas sample, in sequence, through said hydrophobic filter, said first sensor, said first consumable filtration medium, and said second sensor.

* * * * *